(12) United States Patent
Rosheim

(10) Patent No.: US 10,532,458 B2
(45) Date of Patent: Jan. 14, 2020

(54) ROBOTIC MANIPULATOR

(71) Applicant: ROSS-HIME DESIGNS, INCORPORATED, St. Paul, MN (US)

(72) Inventor: Mark E. Rosheim, St. Paul, MN (US)

(73) Assignee: Ross-Hime Designs, Incorporated, St. Paul, MN (US)

( * ) Notice: Subject to any disclaimer, the term of this patent is extended or adjusted under 35 U.S.C. 154(b) by 214 days.

(21) Appl. No.: 15/850,487

(22) Filed: Dec. 21, 2017

(65) Prior Publication Data

US 2018/0111264 A1   Apr. 26, 2018

Related U.S. Application Data

(63) Continuation of application No. 14/882,721, filed on Oct. 14, 2015, now Pat. No. 9,849,586.

(60) Provisional application No. 62/069,032, filed on Oct. 27, 2014.

(51) Int. Cl.
| | |
|---|---|
| *B25J 9/06* | (2006.01) |
| *A61B 34/37* | (2016.01) |
| *B25J 9/00* | (2006.01) |
| *B25J 9/10* | (2006.01) |
| *B25J 17/02* | (2006.01) |
| *A61B 34/30* | (2016.01) |

(52) U.S. Cl.
CPC ............... *B25J 9/06* (2013.01); *A61B 34/37* (2016.02); *B25J 9/0075* (2013.01); *B25J 9/102* (2013.01); *B25J 17/0266* (2013.01); *A61B 2034/305* (2016.02); *Y10S 901/23* (2013.01)

(58) Field of Classification Search
CPC . B25J 9/06; B25J 9/102; B25J 17/0258; B25J 17/0266; A61B 34/30; A61B 34/37; A61B 2034/305
See application file for complete search history.

(56) References Cited

U.S. PATENT DOCUMENTS

| | | | |
|---|---|---|---|
| 2,913,267 | A | 11/1959 | Johnson, Jr. |
| 4,300,362 | A | 11/1981 | Lande et al. |
| 4,489,826 | A | 12/1984 | Dubson |
| 4,821,594 | A | 4/1989 | Rosheim et al. |
| 5,326,369 | A | 7/1994 | Schectman |
| 5,692,412 | A | 12/1997 | Rosheim |
| 6,817,641 | B1 | 11/2004 | Singleton, Jr. |

*Primary Examiner* — William C Joyce
(74) *Attorney, Agent, or Firm* — Kinney & Lange, P.A.

(57) ABSTRACT

A manipulator includes a mount member, a base member with threaded openings and an aperture, two links, and an output member with threaded openings and an aperture. The manipulator also includes three motors mounted to the mount member and three drive trains connected to the motors, respectively.

5 Claims, 35 Drawing Sheets

SECTION A-A

SECTION B-B

SECTION A-A    Fig. 15

SECTION B-B

SECTION A-A

US 10,532,458 B2

ROBOTIC MANIPULATOR

CROSS-REFERENCE TO RELATED APPLICATION(S)

This application is a continuation of U.S. application Ser. No. 14/882,721 filed Oct. 14, 2015 for "Robotic Manipulator" by Mark E. Rosheim, which in turn claims the benefit of U.S. Provisional Application No. 62/069,032 filed Oct. 27, 2014 for "Robotic Manipulator" by Mark E. Rosheim, U.S. Provisional Application No. 62/069,032 is hereby incorporated by reference herein in its entirety.

BACKGROUND

The present invention relates to controlled motion mechanical members used as a mechanical manipulator and, more particularly, to a motion controllable mechanical manipulator having an output member positionable by incrementally operating plural threaded driving shafts.

There is an increasing need for robotic systems capable of placement in, and accurate member positioning operations in, locations characterized by small geometric dimensions of surrounding or nearby material assemblages such as small openings in structures or biological systems. Typically, there is wanted a severing, a removal, or some other reshaping of something within the opening or of something beyond the opening. Of course, such situations can also arise in larger opening systems.

Perhaps the most widely used controlled component in robotic systems is a mechanical manipulator, that portion of a robot used to change the position or orientation of selected objects engaged by that manipulator such as tools to be used in an opening. In many instances, such mechanical manipulators are desired to have capabilities similar to those of the human wrist, or shoulder, that is, exhibiting two or more degrees of freedom of motion.

Although a number of such mechanical manipulators have been developed which to a greater or lesser degree achieve some of these desires therefor, many have been relatively complicated devices requiring complicated components and difficult assembly procedures or both. Many, in addition, represent compromises in having relatively limited range, or singularities within the ranges, or other limitations in performance. Thus, there is a strong desire for a mechanical manipulator which can, under control of the user, position objects very accurately anywhere over at least much of a hemispherical surface without any singularities in the operation of the device in this range, and which can be made very small if so needed and made so inexpensively.

SUMMARY

A manipulator includes a mount member, a base member with threaded openings, a coupling member, and an output member with threaded openings. The manipulator also includes three motors mounted to the mount member and three drive trains connected to the motors, respectively.

DETAILED DESCRIPTION

Figure 1:
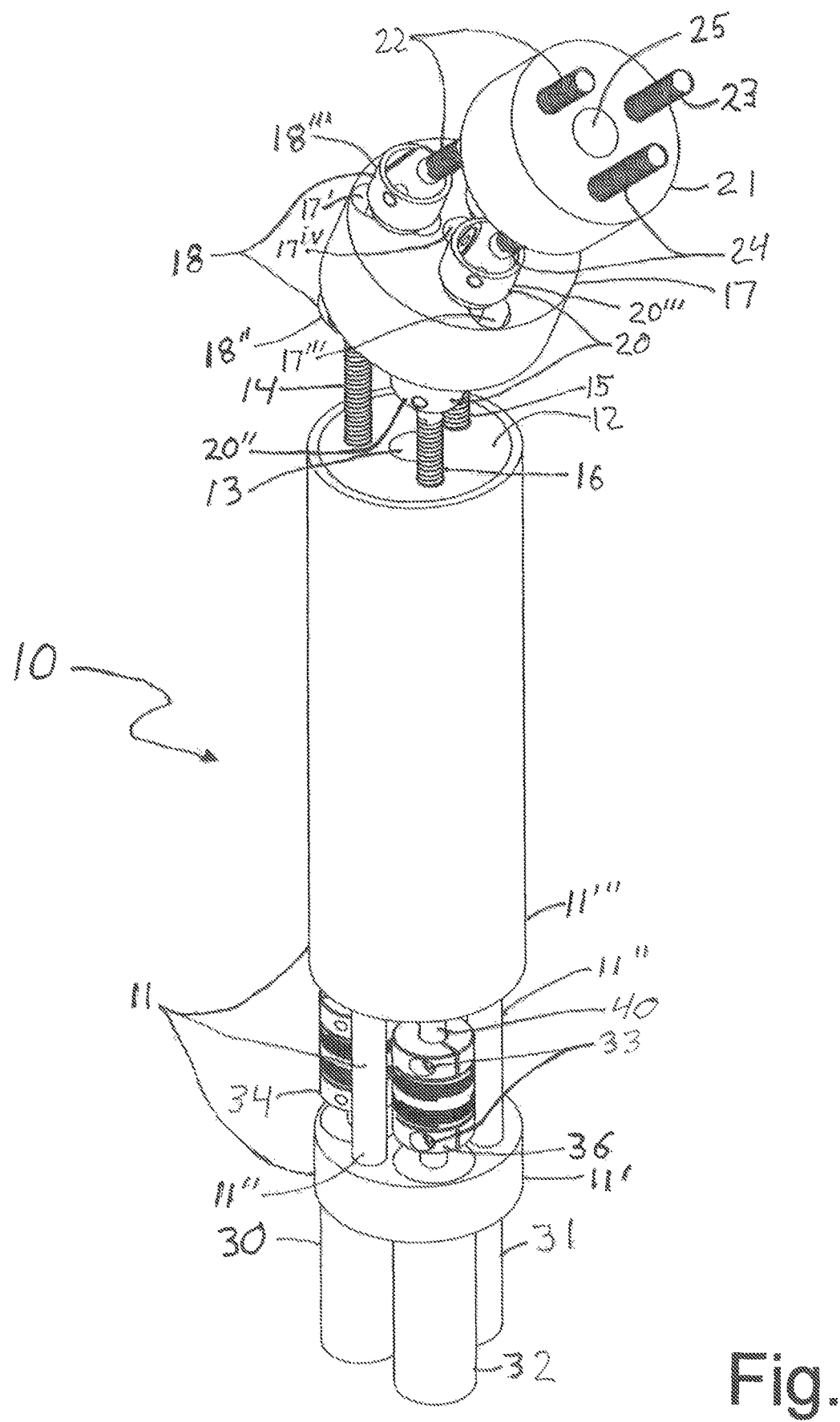
FIGS. 1 through 4 show two perspective views, and elevation and plan views of an embodiment of the present invention.
Figure 2:
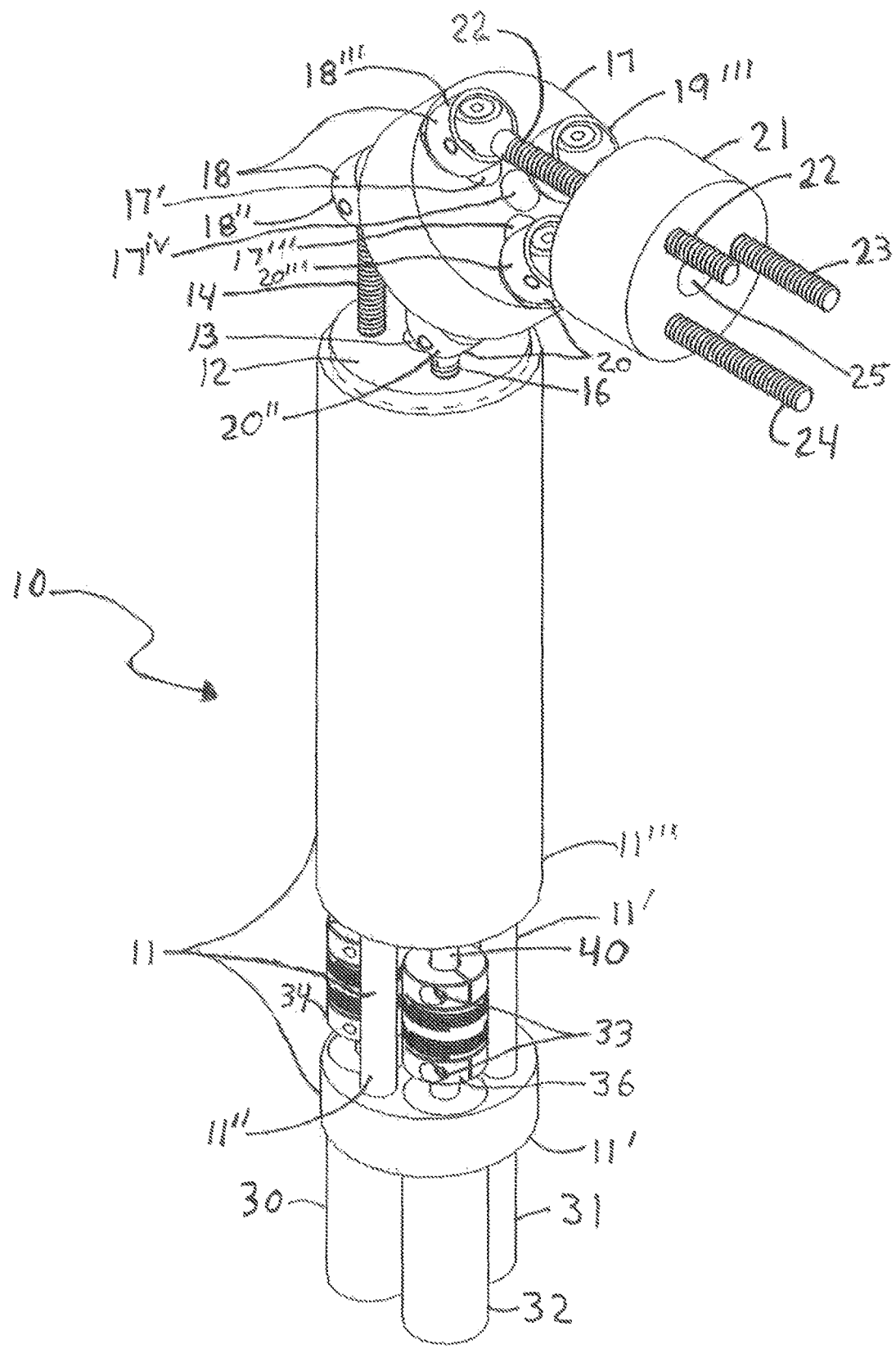
Figure 3:
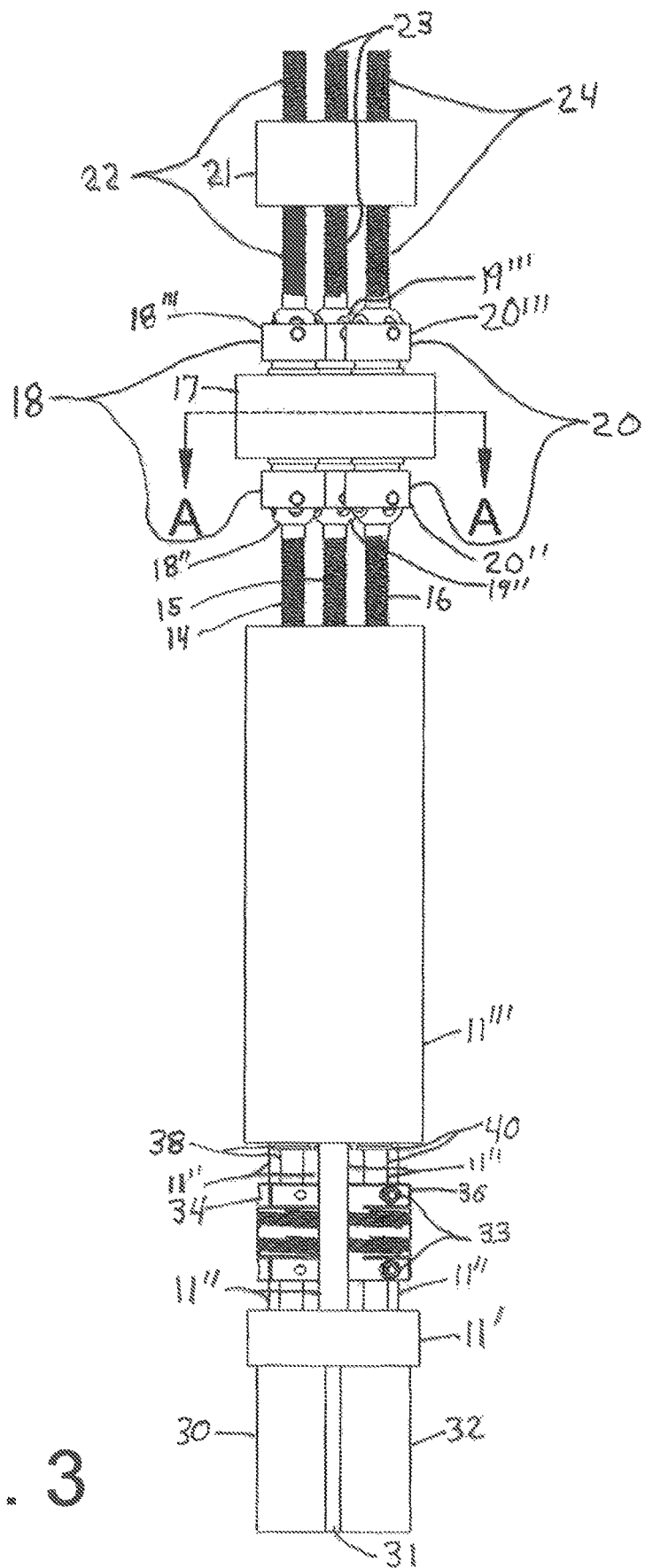
Figure 4:
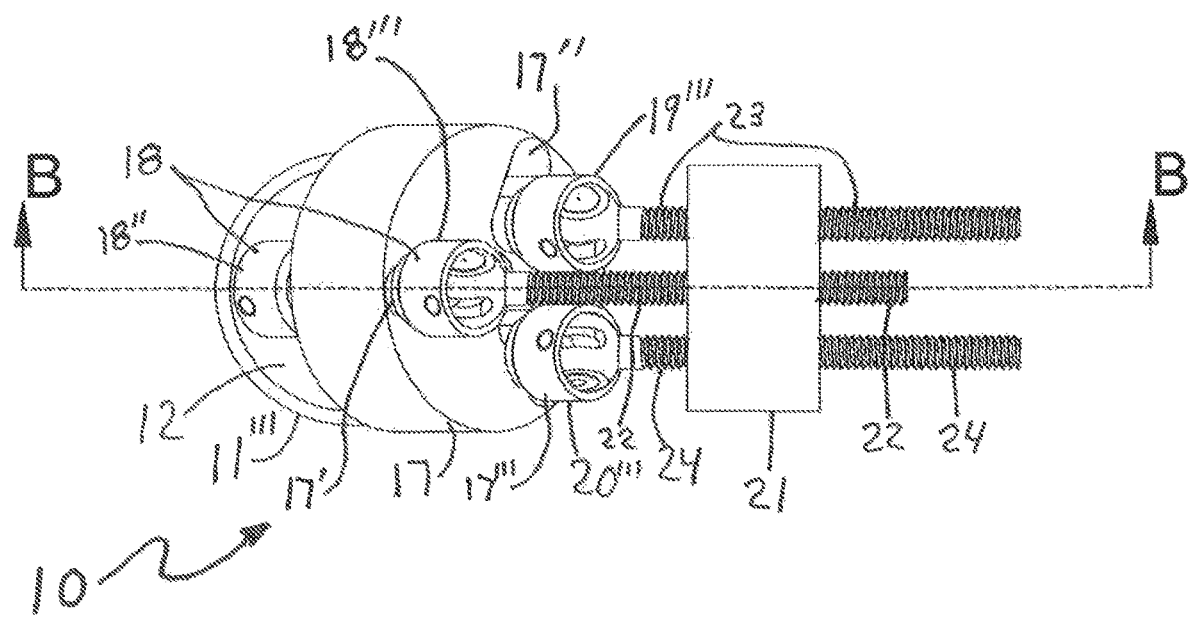

FIGS. 1 through 8 show a first embodiment of a mechanical manipulator, or controlled member motion system, 10, which can have a very large output operating range in various configurations over which it is free of singularities, and over which it can be operated by various force imparting devices directly or through various drive trains. FIGS. 1 and 2 show perspective views of manipulator 10 with an output positionable portion thereof shown in two alternative positions out of many position possibilities. FIG. 3 showing an elevation view with that output portion in a further position, and FIG. 4 shows a plan view of that manipulator.

FIG. 1 shows manipulator 10 having a support and mounting structure, 11, including a motor mounting plate, 11', supported on three posts, 11", with the remainder of robotic manipulator 10 in part surrounded by a protective cylindrical shell sleeve, 11''', positioned intermediately in the manipulator structure. Manipulator 10 further has, in the interior opening of that sleeve, a base plate, 12, affixed in that opening at one end of the sleeve so as to substantially cover the opening. Base plate 12 has three threaded openings through the thickness thereof each at a corner of a centered equilateral triangular pattern formed by these openings on the plate. These threaded openings are spaced apart from an interior opening, 13, also through the thickness of plate 12 that is shown with an exemplary smooth bore. Opening 13 is positioned between the threaded openings and can serve as a conduit for means, such as wires, to together operate a selected output tool as will be subsequently indicated herein.

The three threaded openings in base plate 12 each have a corresponding one of three threaded input shafts, 14, 15 and 16, extending therethrough with each threadedly engaged therewith in either a right-handed or a left-handed threading arrangement. Each of threaded input shafts 14, 15 and 16 extends through base plate 12 to a coupling arrangement in a coupling plate, 17. Each input shaft in this arrangement is connected in a corresponding one of three coupled universal joint pair assemblies, 18, 19 and 20, with each such assembly positioned in and at the coupling plate. Input shaft 14 is connected in coupled universal joint pair assembly 18, input shaft 15 is connected in coupled universal joint pair assembly 19, and input shaft 16 is connected in coupled universal joint pair assembly 20.

The coupling arrangement in coupling plate 17 further extends to an output plate, 21, through having coupled universal joint pair assemblies 18, 19 and 20 in the arrangement each having connected therein a corresponding one of three threaded output shafts, 22, 23 and 24, and with each of these shaft being threadedly engaged with, and extending into or through, a corresponding one of three threaded openings extending through the thickness of this output plate. Again, these threaded openings are spaced apart from an interior opening, 25, through output plate 21 positioned between them that can serve as a conduit for means, such as wires, to together operate a selected output tool as will be subsequently indicated herein, and each threaded opening is at the corner of an equilateral triangle pattern formed by them in this output plate.

Output shaft 22 is connected in coupled universal joint pair assembly 18 and is threadedly engaged in output plate 21 in the opposite threading arrangement to that of the threading arrangement of input shaft 14 in base plate 12. Output shaft 23 is connected in coupled universal joint pair assembly 19 and is threadedly engaged in output plate 21 in the opposite threading arrangement to that of the threading arrangement of input shaft 15 in base plate 12. Output shaft 24 is connected in coupled universal joint pair assembly 20 and is threadedly engaged in output plate 21 in the opposite threading arrangement to that of the threading arrangement of input shaft 16 in base plate 12.

Figure 5:
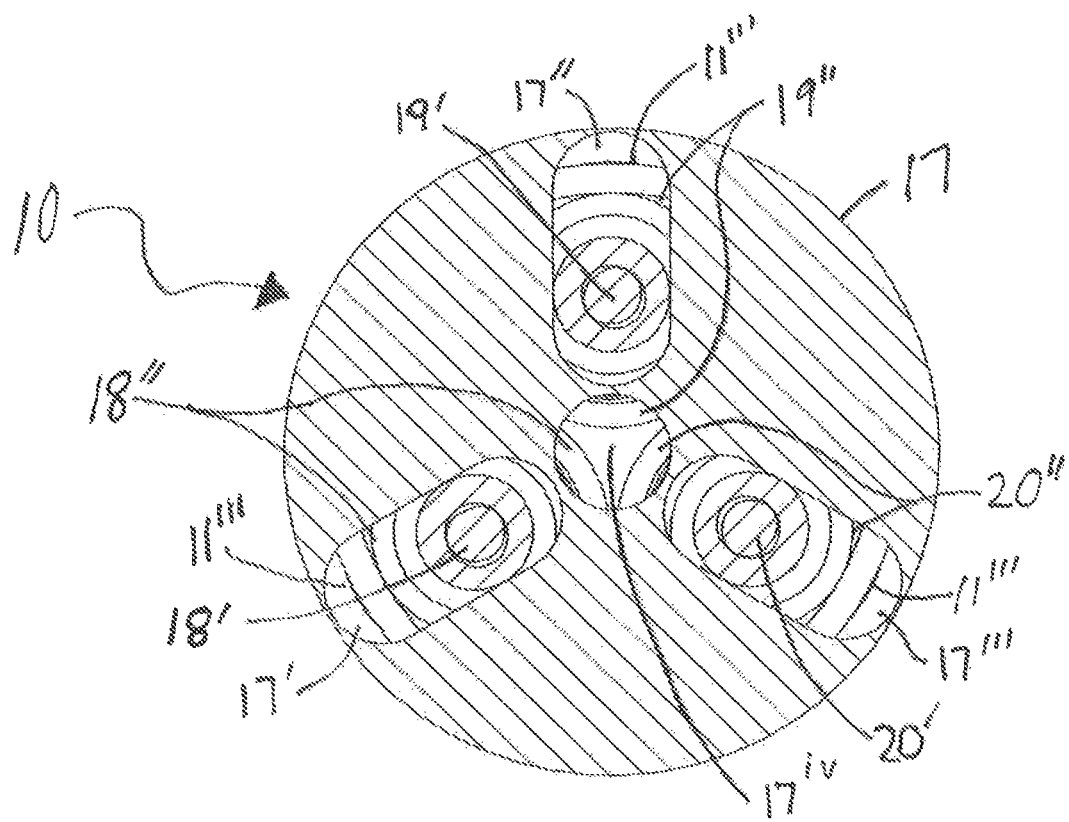
FIG. 5 shows a cross section view of the embodiment shown in FIG. 3.
Figure 6:
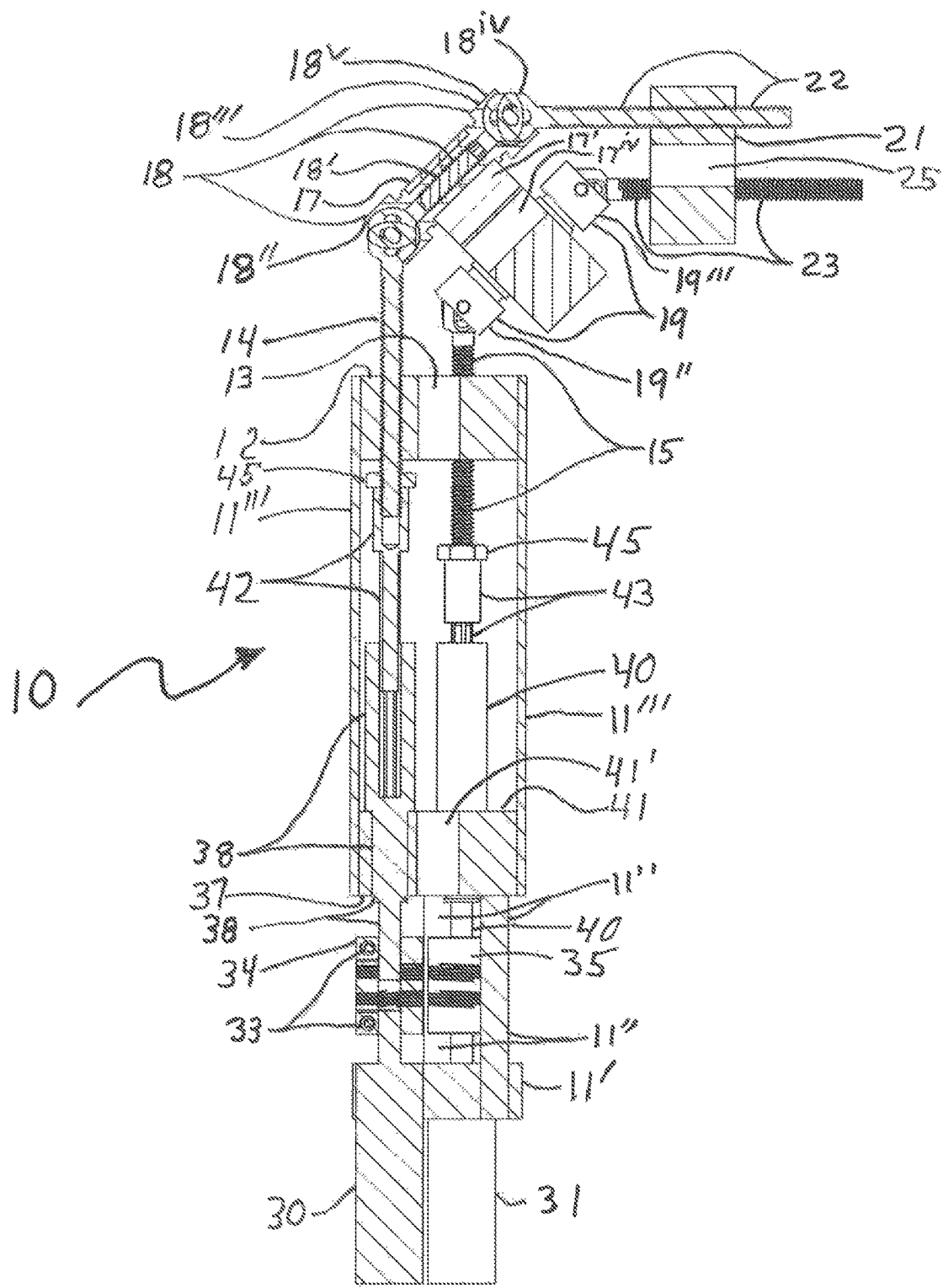
FIG. 6 shows a cross section view of the embodiment shown in FIG. 4.

A cross section view of coupling plate 17 parallel to the lateral extent thereof is shown in FIG. 5 as is indicated in the elevation view of FIG. 3. Further, a cross section view of coupling plate 17 parallel to the thickness thereof is shown in FIG. 6 as is indicated in the top view of FIG. 4. As can be seen in FIGS. 5 and 6, coupling plate 17 has a curved ends oblong slot, 17', extending through the thickness thereof and through which slot a threaded coupling shaft, 18', extends. Shaft 18' is connected on one end thereof to an input universal joint, 18", on the base plate 12 side of plate 17, and connected on the other end thereof to an output universal joint, 18''', on the output plate 21 side of plate 17.

Similarly, coupling plate 17 has a curved ends oblong slot, 17", extending through the thickness thereof and through which slot a threaded coupling shaft, 19', extends to connect on one end thereof to an input universal joint, 19", on the base plate 12 side of plate 17, and to connect on the other end thereof to an output universal joint, 19''', on the output plate 21 side of plate 17. Again, coupling plate 17 has a curved ends oblong slot, 17''', extending through the thickness thereof and through which slot a threaded coupling shaft, 20', extends to connect on one end thereof to an input universal joint, 20", on the base plate 12 side of plate 17, and to connect on the other end thereof to an output universal joint, 20''', on the output plate 21 side of plate 17.

In addition, slots 17', 17" and 17''' are spaced apart from an interior opening, $17^{iv}$, that extends through the thickness of coupling plate 17 and is positioned between these slots. Interior opening $17^{iv}$ can serve, along with openings 13 and 25, as a conduit for means, such as wires, to together operate a selected output tool as will be subsequently indicated herein. The centers of slots 17', 17" and 17''' are each at the corner of an equilateral triangle pattern formed by them in this coupling plate so as to substantially be across from a corresponding one of the threaded openings in base plate 12 and also across from a corresponding one of the threaded openings in output plate 21 if the thickness dimensions of each of these plates are parallel as shown in the elevation view of FIG. 3 where these plates are shown positioned to have the lateral extents of the surfaces thereof parallel to one another.

Figure 7:
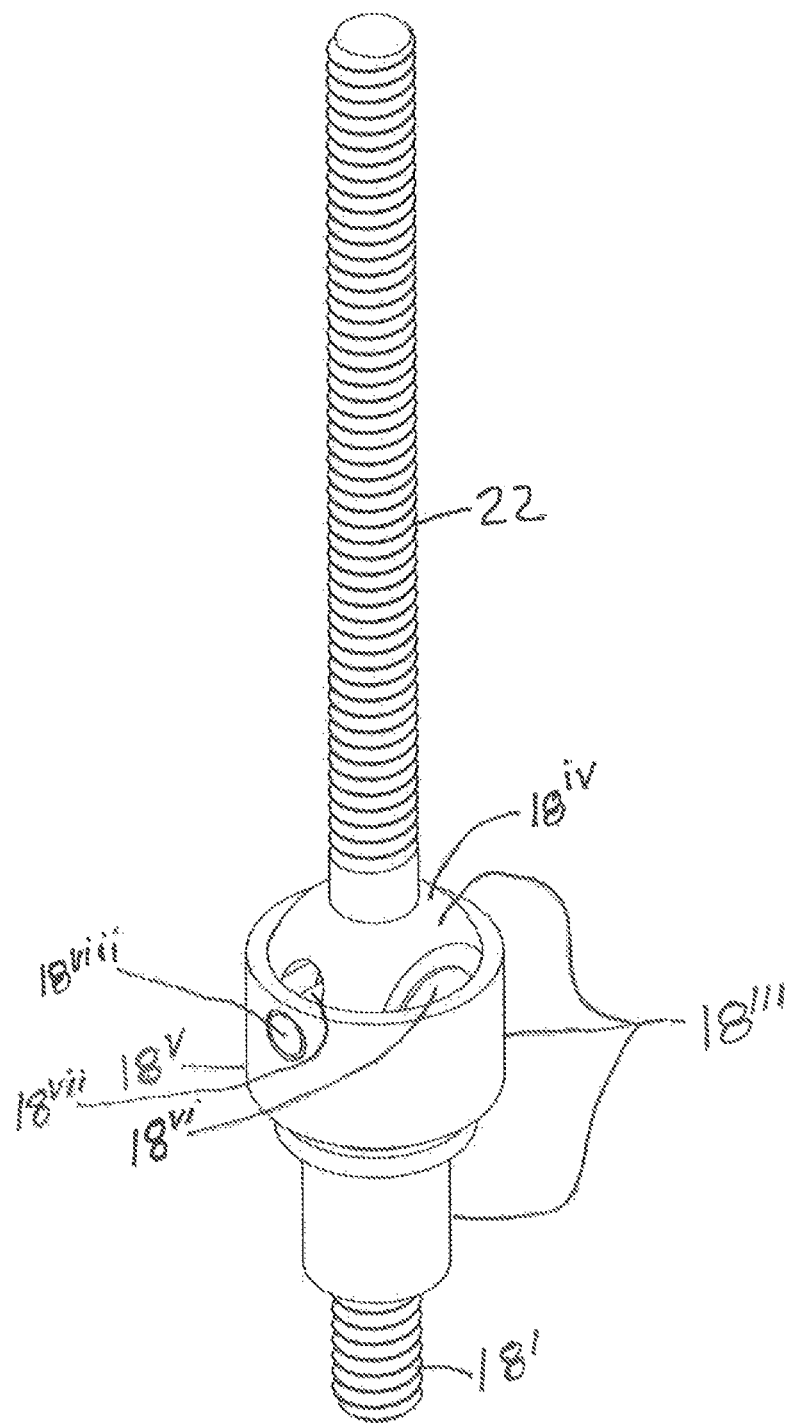
FIG. 7 shows an elevation view of a portion of the embodiment shown in FIG. 6.

Coupled universal joint pair assemblies 18, 19 and 20 are all similarly configured, and the corresponding input and output universal joints in each are also similarly configured. Coupled universal joint pair assembly 18 is shown as an example of these commonly configured assemblies in the cross section view of FIG. 6, and FIG. 7 shows, as an example of these commonly configured universal joints in these assemblies, output universal joint 18'''. Output universal joint 18''' has output threaded shaft 22 affixed in the shell wall of a hollow joint ball, $18^{iv}$, formed as a pierced spherical shell, with this ball positioned in the cup-like opening of a stemmed joint cup, $18^v$, having a pierced cup sidewall. This cup is formed of a larger diameter cylindrical shell with the cup-like opening for receiving joint ball $18^{iv}$, this cup being located at one end of a double cylindrical shell structure. At the opposite end of this double cylindrical shell structure as part of this cup is a coaxially located stem cylindrical shell of a smaller diameter which is interiorly threaded, there being a collar about this stem cylindrical shell near where this smaller diameter cylindrical shell is joined to the larger cup cylindrical shell in the double cylindrical shell structure.

Figure 8:
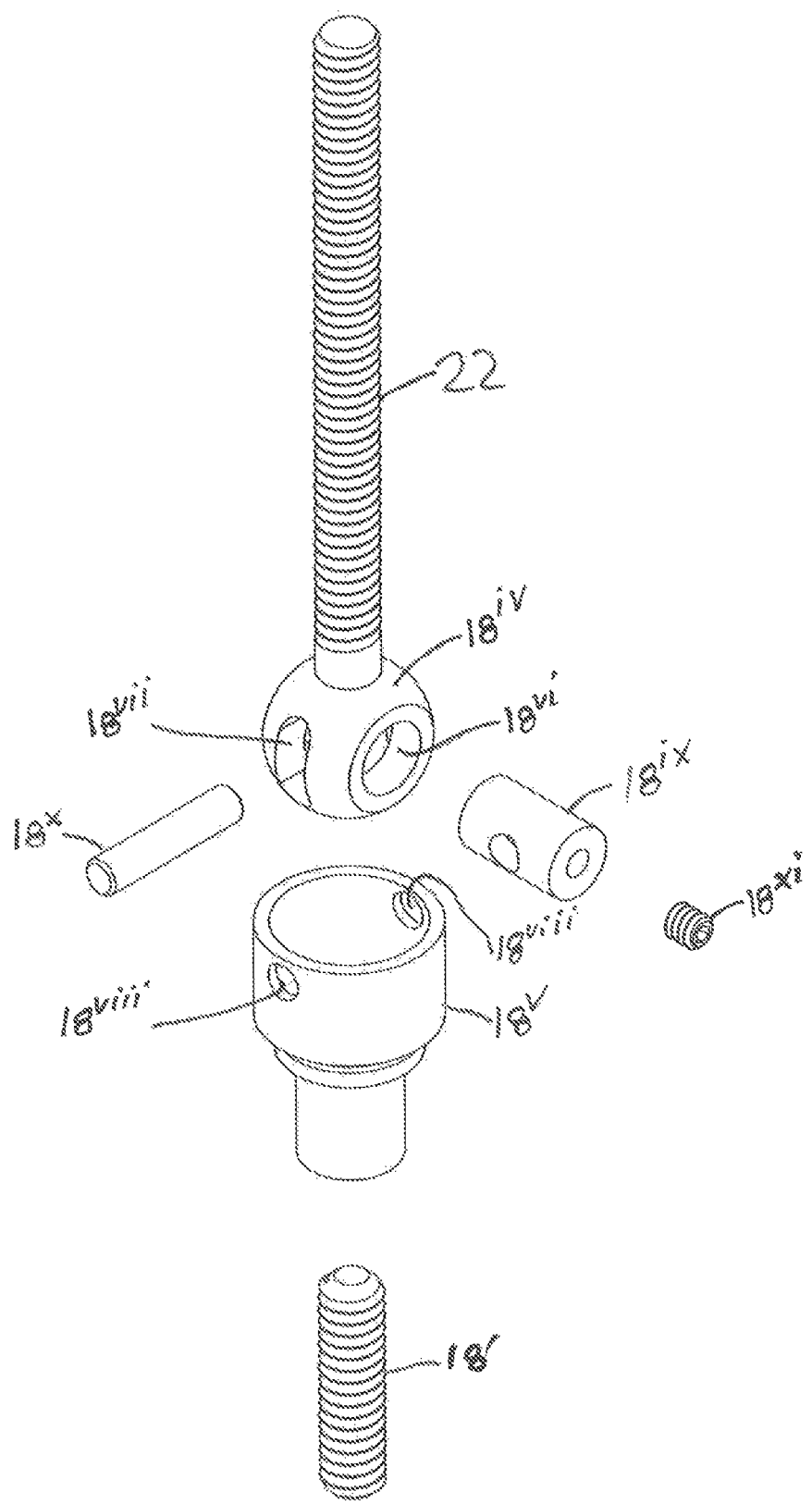
FIG. 8 shows an exploded view of the embodiment portion shown in FIG. 7.

In more detail, with the aid of FIG. 8 showing an exploded view of output universal joint 18''' that is shown assembled in FIG. 7, the shell wall of joint ball $18^{iv}$ is first pierced by an opening therein allowing for the fastening of output shaft 22 therein along a spherical radius, although the shaft could instead be directly attached to the wall without a wall opening being present. This ball shell wall is further pierced by two circular openings, $18^{vi}$, opposite one another along a first spherical diameter perpendicular to the shaft 22 radius. Finally, this shell wall is again pierced by two further slotted openings, $18^{vii}$, opposite one another with each slot beginning where they are each initially closest to shaft 22 along a second spherical diameter there perpendicular to both the radius corresponding to the shaft and the first diameter. These last openings, however, extend in the shell wall from their initial positions into oblong slotted openings in the wall approaching one another at locations relatively far from shaft 22. Their initial positions where these slotted openings begin are along sides of the shell wall across the ball equator (taken with respect to shaft 22) from the shell wall side to which shaft 22 is fastened. In addition, if joint ball 18$^{iv}$ is positioned in the cup-like opening of stemmed joint cup 18v so that the shaft 22 axis is parallel to the common axis of the cup and stem cylindrical shells, these initial slot opening positions on the second diameter of the slotted openings in the ball shell wall, are each across from one of the two opposite sidewall circular openings, 18$^{viii}$, in the sidewall of the cup just inside the cup rim.

A threaded interior cylindrical shell shaft, 18$^{ix}$, is rotatably fitted into the ball shell wall circular openings 18$^{vi}$. Cylindrical shell shaft 18$^{ix}$ has a threaded opening along its axis of symmetry at one end thereof, and further has two circular openings opposite one another along a diameter thereof in the middle of this shaft between its ends into which a solid cylindrical shaft, 18$^{x}$, is fitted that also extends through shell wall slotted openings 18$^{vii}$ and through cup sidewall circular openings 18$^{viii}$. A set screw, 18$^{xi}$, is threadedly engaged with the interior threads of cylindrical shell shaft 18$^{ix}$ through the end of that shaft and tightened against solid cylindrical shaft 18$^{x}$. In this arrangement, output shaft 22 can be rotated to a limited extent about the axis of symmetry of cylindrical shell shaft 18$^{ix}$ in either direction while the shell wall of joint ball 18$^{iv}$ correspondingly rotates past solid cylindrical shaft 18$^{x}$ near to the ends thereof that extend through slotted openings 18$^{vii}$ therein into sidewall circular openings 18$^{viii}$ in the sidewall of stemmed joint cup 18$^{v}$. Output shaft 22 and shell wall of joint ball 18$^{iv}$ can also be rotated in either direction about the axis of symmetry of solid cylindrical shaft 18$^{x}$ that is perpendicular to the axis of symmetry of cylindrical shell shaft 18$^{ix}$.

Thus, any point along output shaft 22 connected to joint ball 18$^{iv}$ in output universal joint 18''' can be positioned in any locations in a limited corresponding spherical surface portion through selected rotations thereof about one or both of these two axes of symmetry established in that joint. Similarly, any points along output shafts 23 and 24 that are similarly connected in similar output universal joints 19''' and 20''', respectively, can be positioned in any respective locations in limited corresponding spherical surface portions.

The stem cylindrical shell of stemmed joint cup 18$^{v}$ is slidably positioned in slot 17' of coupling plate 17 as far as the collar thereabout permits. There, threaded coupling shaft 18', which is threadedly engaged in this stem cylindrical shell, joins it to the stem cylindrical shell of the stemmed joint cup of input universal joint 18" by being threadably engaged in this second stem cylindrical shell. Input universal joint 18" is also slidably positioned in slot 17' of coupling plate 17 from the other side of this plate to the extent allowed by its collar as seen in FIG. 6. Threaded coupling shaft 18' fixedly joins these two stem cylindrical shells so that any rotation of the stemmed joint cup of input universal joint 18" along its common axis results in similarly rotating both that shaft along its axis of symmetry and stemmed joint cup 18$^{v}$ of output universal joint 18''' in slot 17' of coupling plate 17 along its common axis. Thus, coupled universal joint pair assembly 18 can be rotated as a unit in slot 17' along the axis of symmetry of threaded coupling shaft 18' and, similarly, coupled universal joint pair assemblies 19 and 20 can be rotated as units in slot 17" and 17''', respectively.

Any rotations of the output shafts about the axes of symmetry in the output universal joints in which they are connected cause corresponding motions of output plate 21 in which these shafts are threadedly engaged to result in changes in the plate orientation. Such output plate reorientations are accomplished by selectively changing the lengths of these output shafts between coupling plate 17 and plate 21 through such rotating of those shafts since this latter plate in this manner has degrees of freedom in its motion in robotic manipulator 10 with respect to plate 17 (and so also with respect to base plate 12 as will be described below). Input shafts 14, 15 and 16, similarly connected in similar input universal joints 18", 19" and 20", respectively, will, if rotated about the corresponding axes of symmetry therein, cause such rotations of the output shafts in output universal joints 18''', 19''' and 20''' but will result in changing the lengths of these input shafts between coupling plate 17 and base plate 12 to thereby reorient this coupling plate.

More particularly, plate 12, typically being a fixed position reference for any manipulations in robotic manipulator 10, leads to any rotations of input shafts 14, 15 and 16 threadedly engaged therein causing corresponding changing of the lengths of these input shafts between it and coupling plate 17 and further leads to the joint cups in the corresponding input universal joints rotating about the corresponding one of the joint balls connected to those shafts. The changing lengths of the input shafts between plates 12 and 17 causes corresponding reorientations of plate 17 with respect to fixed plate 12. The rotating of the corresponding joint balls connected to those shafts in the input universal joints rotates the corresponding rotatably connected joint cups that are slidably positioned across and partially in the slots of coupling plate 17, forcing the corresponding joint cups in the in the output universal joints in the coupled universal joint pair assemblies 18, 19 and 20, also slidably positioned across and partially in the slots of coupling plate 17, to together rotate as then also do the joint balls rotatably connected thereto in those output universal joints.

Output plate 21, threadedly engaged with output shafts 22, 23 and 24 that are connected the joint balls in the output universal joints in the universal joint pair assemblies 18, 19 and 20, must also change orientations with corresponding changes in orientation of plate 17 as the lengths of these output shafts between plates 71 and 21 change with the resulting rotations of the output shafts. Slots 17', 17" and 17''' in coupling plate 17 allow radial sliding movements therein of the corresponding one of coupled universal joint pair assemblies 18, 19 and 20 having portions thereof extending therethrough so that these assemblies can make any slight radial position changes needed thereof as coupling plate 17 rotates to follow the corresponding ones of the ends of the input and output shafts during reorientations of coupling plate 17 and output plate 21.

These positioning capabilities of output shafts 22, 23 and 24, in conjunction with the positioning of coupling plate 17 by selected rotations of input shafts 14, 15 and 16, provide the capability for an operator of robotic manipulator 10 to control the angular position of output plate 21 through selected rotation operations on these input shafts along the shaft axes. Such rotation operations first force the ball joint end of the input shaft being so rotated to selectively be either further away from, or closer to, base plate 12, i.e. increasing or decreasing the length of that shaft between coupling plate 17 and base plate 12. These changes occur through the shaft being selectively rotated, including its threads, in one direction, to be further through base plate 12 to have its end further from that plate, i.e. to be "screwed" further through that plate. Alternatively, that shaft, by being withdrawn through a shaft rotation in the opposite direction will have that end rendered to extend less far through that plate. If, for example, a right-handed thread arrangement is chosen for the input shafts as engaged in base plate 12, a clockwise rotation of an input shaft at the side of base plate 12 farthest from coupling plate 17 will result in that input shaft extending further through plate 12. This extension thereby forces the portion of coupling plate 17 where that input shaft is connected in a coupled universal joint pair assembly to become farther away from the part of base plate 12 adjacent that input shaft. Such an additional extension of an input shaft through base plate 12 from the length of its extension shown in FIG. 3 can be seen for input shaft 14 in FIGS. 1, 2 and 6.

Furthermore, these clockwise rotations of input shafts also forces the corresponding one of coupled universal joint pair assemblies 18, 19 and 20 to rotate within its slot in coupling plate 17. Thus, for input shaft 14, coupled universal joint pair assembly 18 must rotate with in slot 17' as input shaft 14 rotates. Input shaft 14 rotates the joint ball of input universal joint 18" to in turn rotate the joint cup positioned about this ball in this universal joint in slot 17', and so also rotate attached threaded coupling shaft 18' in this slot. The rotation of threaded coupling shaft 18' in turn rotates joint cup 18$^v$ of output universal joint 18''' in this slot, which causes joint ball 18$^{iv}$ therein to rotate in this universal joint. Rotating joint ball 18$^{iv}$ results in the rotation of the corresponding output shaft connected to joint ball 18$^{iv}$ in output universal joint 18''', output shaft 22.

If, however, input shaft 14 is in a right-handed thread arrangement in base plate 12, output shaft 22 must be in the opposite thread arrangement in output plate 21. If otherwise output shaft 22 was in a right-handed thread arrangement in output plate 21, the clockwise rotation would extend this output shaft further through output plate 21 thus drawing the portion adjacent output shaft 22 closer to coupling plate 17, and thereby canceling some of the rotation effect on coupling plate 17 obtained by adding to the length of input shaft 14 between coupling plate 17 and base plate 12. A left-handed thread arrangement between output shaft 22 and output plate 21 will, for a clockwise rotation thereof resulting from a clockwise rotation of input shaft 14, withdraw some of the extension of output shaft 22 that had been beyond output plate 21 to thereby increase the length of output 22 between output plate 21 and coupling plate 17. This will add to the rotation of output plate 21 with respect to coupling plate 17 from that provided by the rotation of plate 17, and thus further increase the rotation of output plate 21 with respect to base plate 12. Rotation of input shafts 15 and 16 along the axes of symmetry thereof, and so of coupled universal joint pair assemblies 19 and 20 and output shafts 23 and 24 correspondingly connected thereto, will, for the same threading arrangements for input shafts 15 and 16 used with input shaft 14, will similarly cause similar reorientations of plates 17 and 21. The angle achieved between output plate 21 and coupling plate 17 matches the angle obtained between coupling plate 17 and base plate 12.

Figure 9:
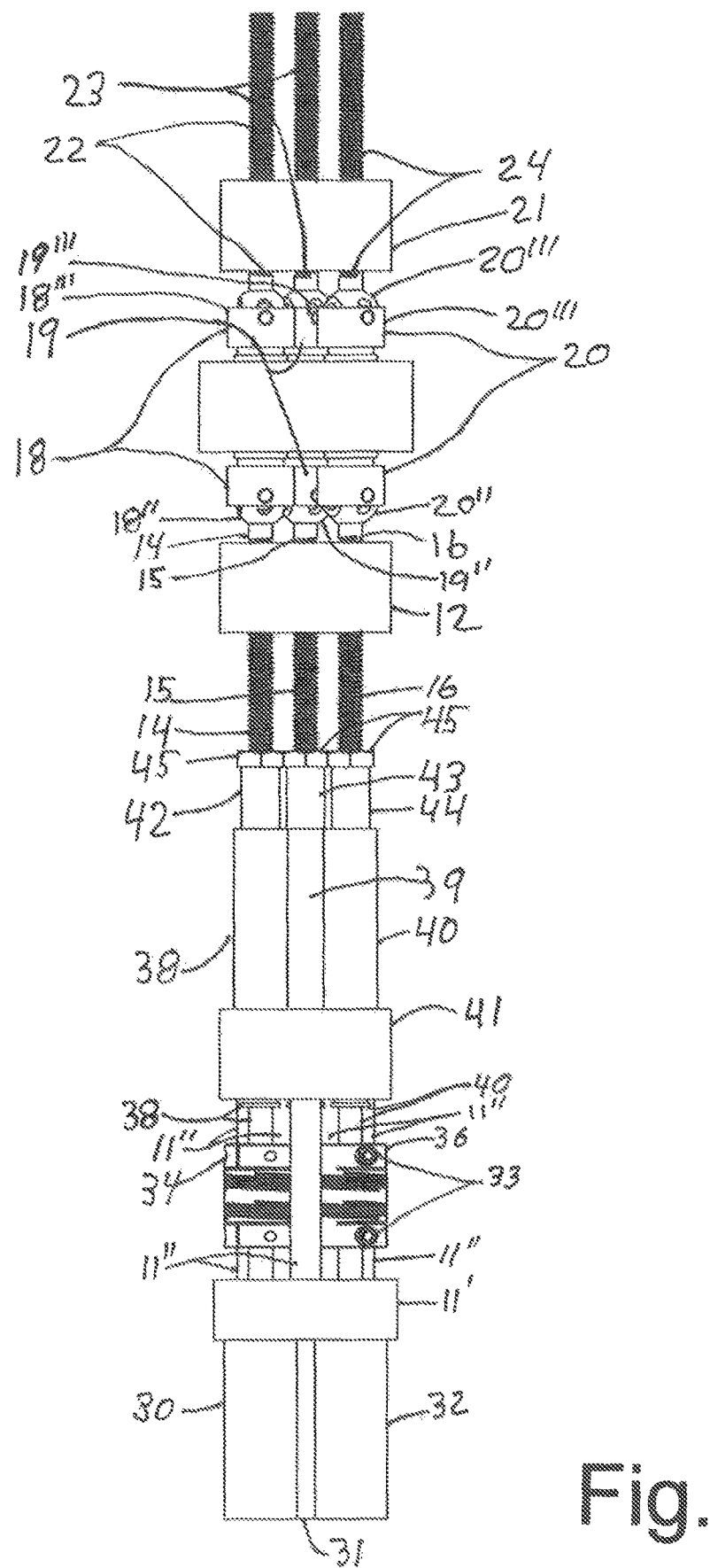
FIGS. 9 and 10 show alternative positions for a portion of the embodiment shown in FIG. 3 as modified to further expose inner structure.
Figure 10:
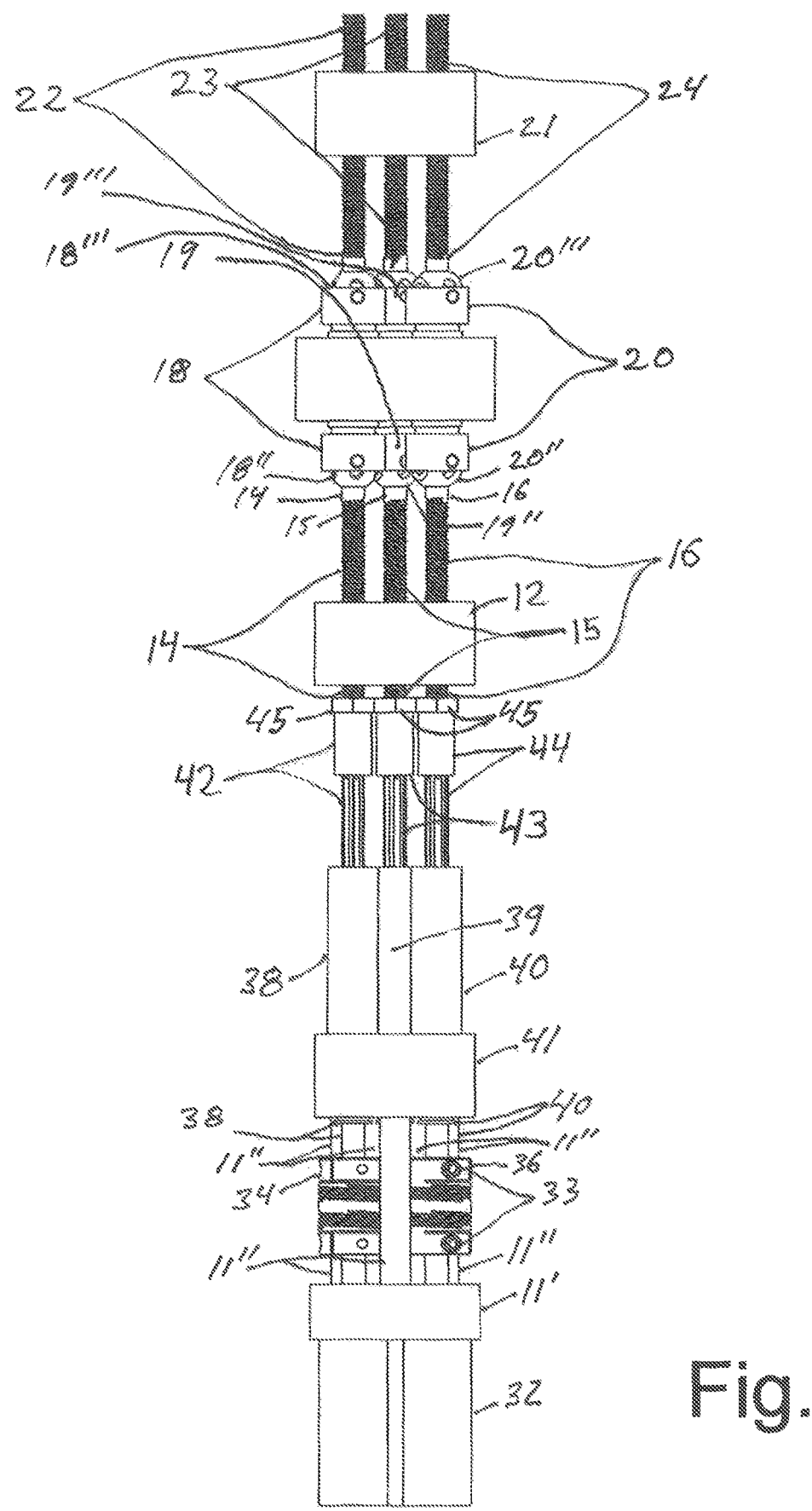

Selected rotations of input shafts 14, 15 and 16 in various combinations thereof can thus result in selected reorientation alternatives of plates 17 and 21 over a large range of spatial orientations, and so provide selected radial position alternatives for these plates. As examples, FIGS. 9 and 10 show the embodiment of robotic manipulator 10 shown in FIG. 3 with coupling plate 17 and output plate 21 in the same orientations with respect to base plate 12 in all three figures, but with cylindrical shell sleeve 11''' omitted in FIGS. 9 and 10.

Figure 11:
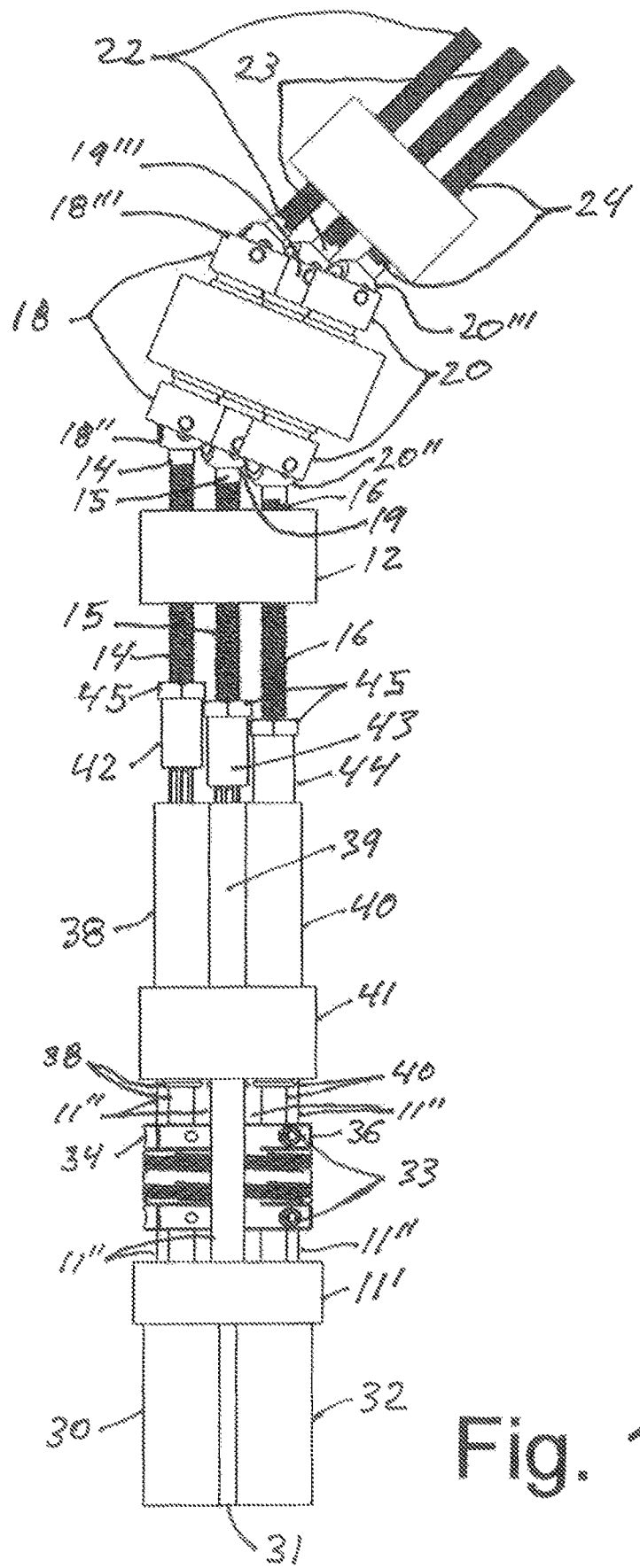
FIG. 11 shows an alternative position for a portion of the embodiment shown in FIG. 1 as modified to further expose inner structure.

However, the radial extent of output plate 21 away from base plate 12 differs in these figures despite the same orientations thus demonstrating that rotation of the output shafts of motors 30, 31 and 32 can be chosen to control to a degree such radial extent. Again, in FIG. 11, the embodiment of robotic manipulator 10 is shown with coupling plate 17 and output plate 21 in the same orientations with respect to base plate 12 as shown in FIG. 1, but with cylindrical shell sleeve 11''' omitted in FIG. 11. A different extent of output plate 21 along the angular direction chosen for that output plate with respect to base plate 12 is shown is FIG. 11 from that shown in FIG. 1 which differences are selectable through selecting corresponding rotations for motors 30, 31 and 32.

Figure 12:
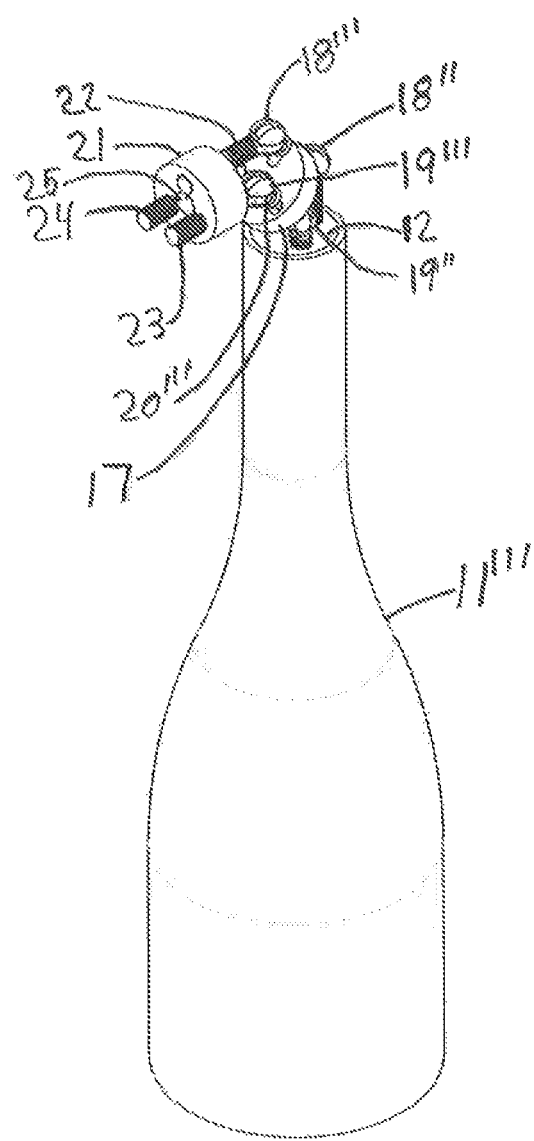
FIG. 12 shows a protectively shielded example of the embodiments otherwise shown in FIGS. 1 through 6 and 9 through 11.

The selected rotations of manipulator input shafts 14, 15 and 16 are provided by corresponding selected rotation operations of each of a set of three motors, 30, 31 and 32, typically electric motors, provided at a control location behind base plate 12 with respect to coupling plate 17 provided on the other side of plate 12. These motors are each connected through a corresponding drive train to a corresponding one of these input shafts as shown in FIGS. 1, 2, 3 and 6. Thus, motor 30 is mounted in motor mounting plate 11' and coupled to input shaft 14, motor 31 is mounted in motor mounting plate 11' and coupled to input shaft 15, and motor 32 is mounted in motor mounting plate 11' and coupled to input shaft 16. Protective cylindrical shell sleeve 11''' of FIGS. 1, 2, 3 and 6 can be extended in length downward in the drawings to also provide a protective shield about these motors and drive trains as seen in FIG. 12, and the sleeve bottom end can then be joined to a manipulator mounting plate across the bottoms of the motors, typically provided parallel to base plate 12 (not shown), or to some other mounting arrangement.

Thus, the output shaft of each of the motors at the beginning of a corresponding drive train is fastened in a drive train beam coupler (although other kinds couplers could be used) using one of a pair of set screws, 33, and connected by that coupler to the drive train first cup and shaft driver which is rotatably coupled next to the drive train second cup and shaft driver that is connected in turn to a manipulator input shaft extending thereto from base plate 12. As seen in FIGS. 1, 2, 3 and 6, the output shaft of motor 30 is positioned within a beam coupler, 34, extending into it from one split ring end thereof and held there by one set screw in a pair 33 thereof that joins the threaded openings across the ring split from one another. The output shaft of motor 31 is positioned within a beam coupler, 35, extending into it from one split ring end thereof and held there by one set screw in a pair 33 thereof that joins the threaded openings across the ring split from one another. The output shaft of motor 32 is positioned within a beam coupler, 36, extending into its central opening from one split ring end thereof, and held there by one set screw in a pair 33 thereof that joins the threaded openings provided across the ring split ends from one another.

Beam couplers are used to allow for assembly misalignments between the motor output shafts and the subsequent drive train components. They are formed as a cylindrical shell with split rings at each end all about a central opening, and are made from a single piece of material to eliminate backlash from torque transmissions. They have two spiral cuts therein extending from the shell outside surface to the surface surrounding the central opening with the cuts being positioned on either side of the halfway point in the cylinder length, and they allow lateral bending to accommodate misalignment and while being yet able to transmit torque.

The split ring at the opposite end of each beam coupler has the shaft of the corresponding drive train first cup and shaft driver extending therethrough into the coupler central opening opposite the corresponding motor shaft, and held there by the remaining one of the corresponding pair of set screws 33. Each first cup and shaft driver has a two part shaft coaxially formed with a cup at one end thereof, the cup having interior splines parallel to the common axis. The shaft of the first cup and shaft driver has a smaller diameter first part that is positioned in the central opening of the coupler and that joins on the common axis to the end of the shaft second part, having a larger diameter and that is positioned in a corresponding one of three bushings, 37, (which could instead be bearings), this joining of shaft parts being through a collar of a slightly larger diameter about the second part and that is positioned where the shaft parts are joined. This shaft second part is in turn joined at its opposite end to the outside of the closed end of the cup again on the common axis, the outside diameter of the cup being greater than the diameters of the shaft second part and its collar.

As seen in FIG. 3, and in part in FIGS. 1, 2 and 6, beam coupler 34 has the smaller shaft diameter portion of a first cup and shaft driver, 38, extending into its central opening through the remaining split end thereof and held there by the remaining set screw in the corresponding pair 33 thereof that joins the threaded openings provided across the ring split ends from one another. Beam coupler 35 has the smaller shaft diameter portion of a first cup and shaft driver, 39, extending into its central opening through the remaining split end thereof and held there by the remaining set screw in the corresponding pair 33 thereof that joins the threaded openings provided across the ring split ends from one another. Beam coupler 36 has the smaller shaft diameter portion of a first cup and shaft driver, 40, extending into its central opening through the remaining split end thereof and held there by the remaining set screw in the corresponding pair 33 thereof that joins the threaded openings provided across the ring split ends from one another.

Bushings 37 are each positioned in a corresponding opening in a bushing plate, 41, such that the cup of each of first cup and shaft drivers 38, 39 and 40 each have a portion of its bottom positioned against its corresponding bushing 37. Bushings 37 in plate 41 are spaced apart from an interior opening, 41', through output plate 41 positioned between them that can serve as a conduit for means, such as wires, to together operate a selected output tool as will be subsequently indicated herein, and each bushing is at the corner of an equilateral triangle pattern formed by them in this bushing plate.

The splined interior of each of the cups of first cup and shaft drivers 38, 39 and 40 has the splined shaft of the corresponding drive train second cup and shaft driver engaged therein. Each second cup and shaft driver has the other end of the splined shaft part thereof coaxially joined with the closed end of a cup of a larger outside surface diameter, this cup having interior threading therein. Each of these cups of the second cup and shaft drivers have a corresponding one of manipulator shafts 14, 15 and 16 threadedly engaged therein.

As seen in FIG. 6, first cup and shaft driver 38 has the splined shaft of a second cup and shaft driver, 42, engaged in the interior splines of its cup, and this second cup and shaft driver 42 further has threaded input shaft 14 engaged with the threads inside its cup. Not seen in FIG. 6 (or in the other figures) is first cup and shaft driver 39 and a corresponding second cup and shaft driver, 43, because of being blocked in that view by first cup and shaft driver 40 and a corresponding second cup and shaft driver, 44. Nevertheless, first cup and shaft driver 39 has the splined shaft of second cup and shaft driver 43 engaged in the interior splines of its cup, and this second cup and shaft driver 43 further has threaded input shaft 15 engaged with the threads inside its cup. First cup and shaft driver 40 has the splined shaft of second cup and shaft driver 44 engaged in the interior splines of its cup, and this second cup and shaft driver 44 further has threaded input shaft 16 engaged with the threads inside its cup. Each of manipulator input shafts 14, 15 and 16 has a corresponding one of three nuts, 45, threadedly engaged with it that is tightened the cup of the corresponding one of the second cup and shaft drivers in which it is threadedly engaged to hold that input shaft in a fixed position in that cup. Thus, rotation of the output shafts of any motors 30, 31 or 32 will cause, through the corresponding drive train, a corresponding rotation of the corresponding one manipulator input shafts 14, 15 and 16.

The components of robotic manipulator 10 can be formed of steel or stainless steel for general uses, although bushing material will typically be of a softer metal such as bronze. Specialized uses may require special materials. As an example, use of robotic manipulator 10 in a high magnetic field environment, permeable material is unsatisfactory. Instead, in such a situation, the components could be made of Macor, a machineable glass-ceramic material, or of zirconia, i.e. zirconium dioxide.

Figure 13:
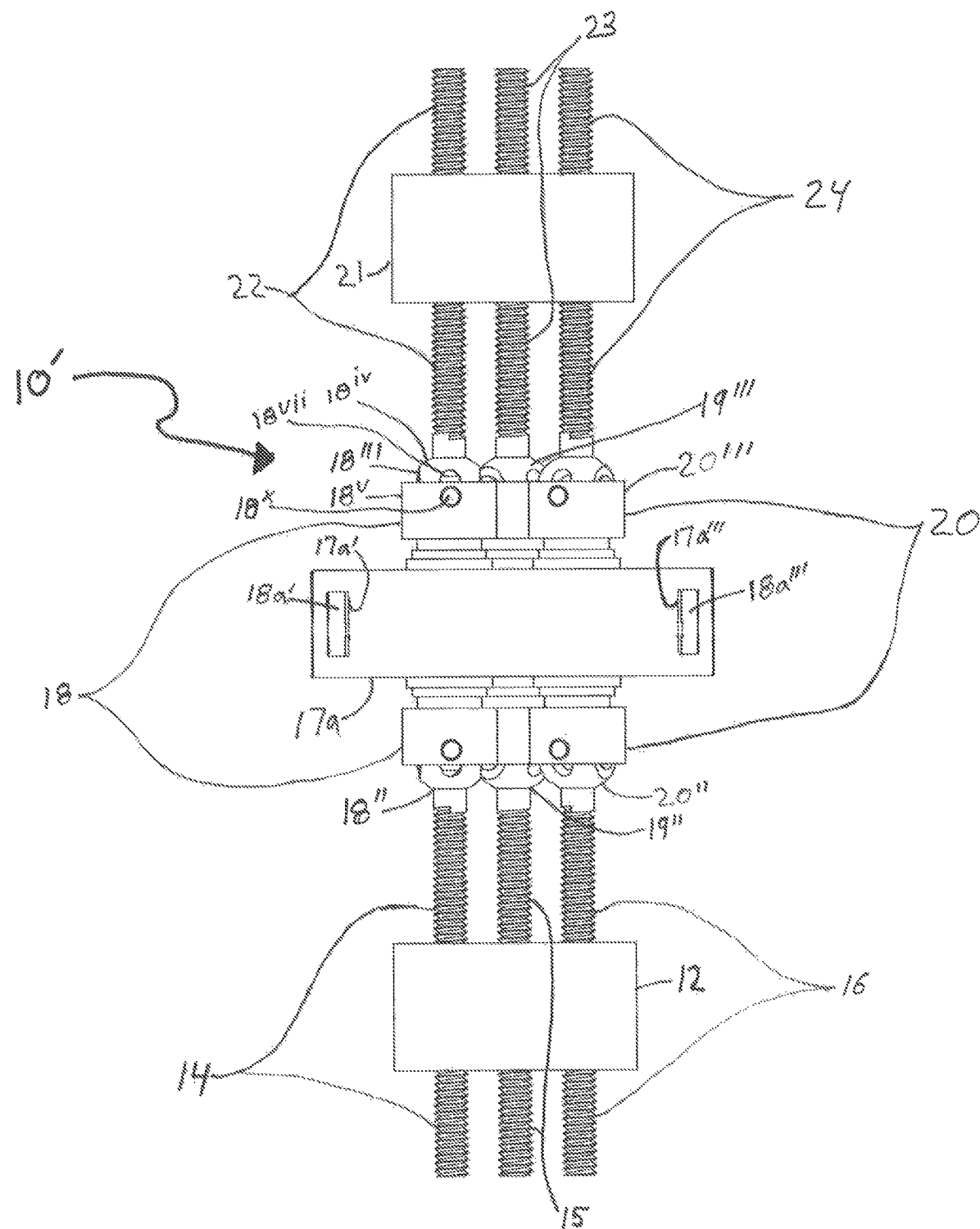
FIGS. 13 and 14 show elevation and plan views of another embodiment of the present invention.
Figure 14:
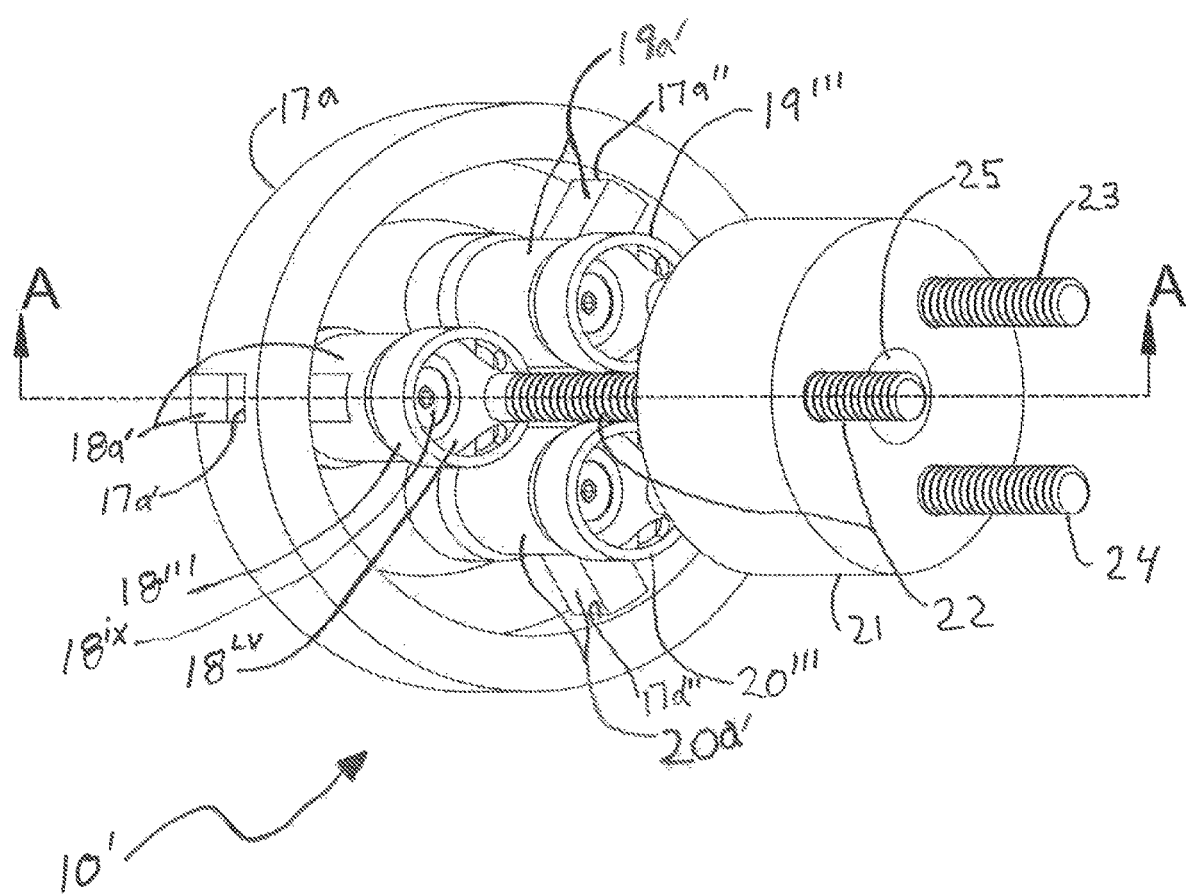
Figure 15:
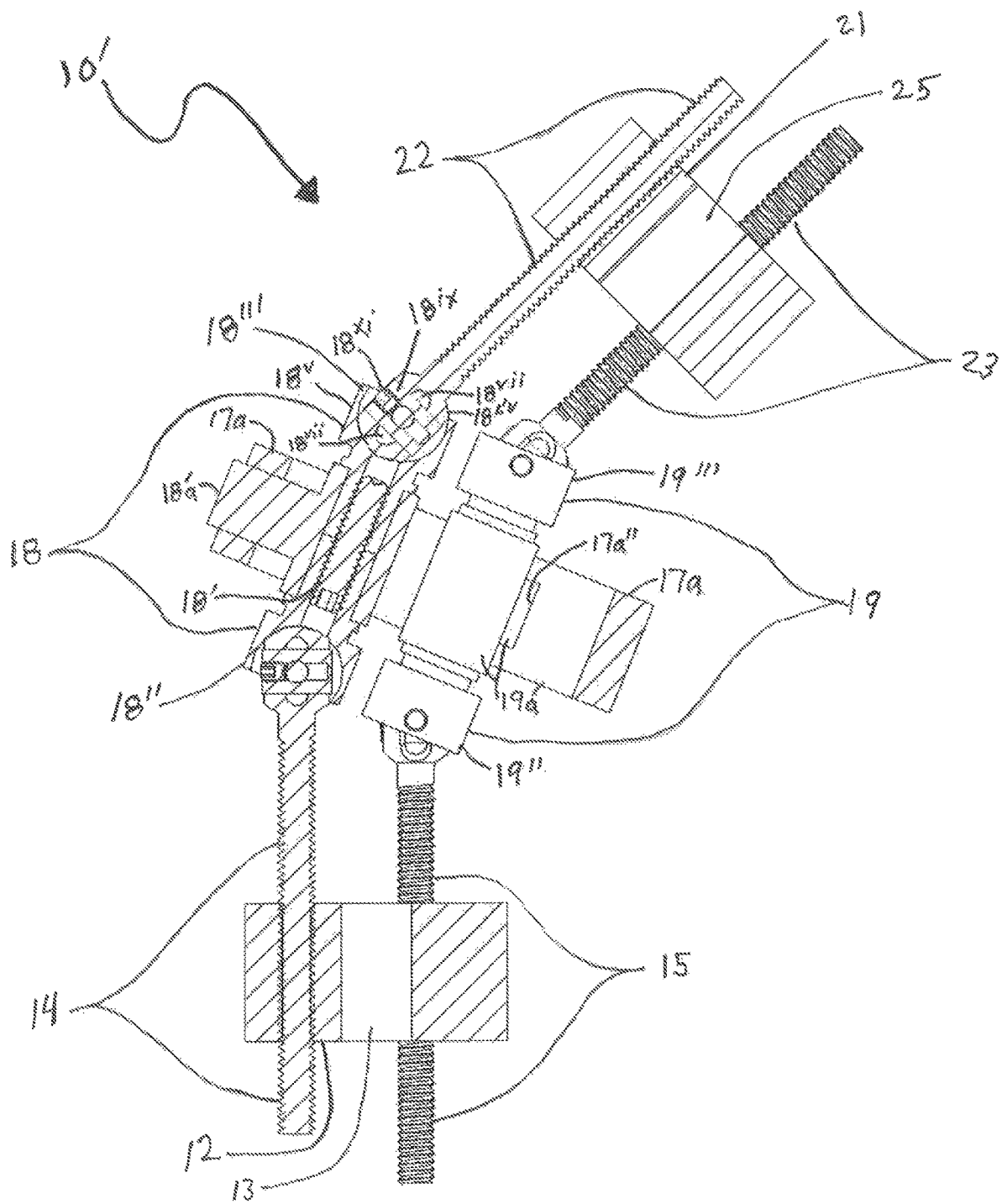
FIG. 15 shows a cross section view of the embodiment shown in FIG. 14.

Alternative variations of robotic manipulator 10 shown in FIGS. 1 through 12 can provide additional capabilities or more economical implementation, or both, at least in some circumstances. Thus, coupling plate 17 of robotic manipulator 10 is shown replaced by a perforated coupling ring, 17a, with three rectangular openings, 17a', 17a" and 17a''', and three cylindrical shell and block T-bar holders, 18a', 18a" and 18a''' in a further robotic manipulator, 10' as shown in the elevation view in FIG. 13, the plan view of FIG. 14, and the cross section view in FIG. 15. Parts in robotic manipulator 10' similar to those in robotic manipulator 10 have the same designators in each of their respective drawings. A portion of robotic manipulator 10' is shown in selected alternative orientations in these two figures, and the motors and drive trains for this manipulator, identical or similar to those for robotic manipulator 10, have been omitted in them.

Perforated coupling ring 17a has rectangular openings 17a', 17a" and 17a''' equally angularly spaced about the ring sidewall, and which extend through that sidewall so as to each be equally spaced from the sidewall ends. Each of coupled universal joint pair assemblies 18, 19 and 20 has a corresponding one of the three cylindrical shell and rectangular block T-bar holders 18a', 19a' and 20a' added thereto with the cylindrical shell portion of each holder surrounding a central part of the corresponding assembly. The rectangular block portion of each such T-bar holder has an end thereof joined to the cylindrical shell portion of the holder and the other end thereof extending in, and sometimes selectively through, a corresponding one of rectangular openings 17a', 17a" and 17a'''.

Thus, assembly 18 has the cylindrical shell portion of T-bar holder 18a' positioned about shaft 18' and the stems of the stemmed joint cups in input universal joint 18" and in output universal joint 18''', but between the collars of these cups, and has the rectangular portion thereof, fastened to that cylindrical shell portion, extending through opening 17a'. Assembly 19 has the cylindrical shell portion of T-bar holder 19a' positioned about shaft 19' and the stems of the stemmed joint cups in input universal joint 19" and in output universal joint 19''', again between the collars of these cups, and has the rectangular portion thereof, fastened to that cylindrical shell portion, extending through opening 17a''. Finally, assembly 20 has the cylindrical shell portion of T-bar holder 20a' positioned about shaft 20' and the stems of the stemmed joint cups in input universal joint 20'' and in output universal joint 20''', once again between the collars of these cups, and has the rectangular portion thereof, fastened to that cylindrical shell portion, extending through opening 17a'''.

Rotation of input shafts 14, 15 and 16 along the axes of symmetry thereof, and so of coupled universal joint pair assemblies 18, 19 and 20 and output shafts 22, 23 and 24 correspondingly connected thereto, will, for the same threading arrangements for input shafts 14, 15 and 16 used previously in manipulator 10, will similarly cause similar reorientations of plates 17 and 21. That is, selected rotations of input shafts 14, 15 and 16 in various combinations thereof can again result in selected reorientation alternatives of plates 17 and 21 over a large range of spatial orientations to thus provide selected radial position alternatives for these plates. Rectangular openings 17a', 17a'' and 17a''' in coupling ring 17a allow lateral sliding movements therein of the rectangular block portion of the corresponding one of T-bar holders 18a', 19a' and 20a' each supporting corresponding one of coupled universal joint pair assemblies 18, 19 and 20 so that these assemblies can make any slight radial position changes needed therefor as coupling ring 17a rotates to follow the corresponding ones of the ends of the input and output shafts during reorientations of coupling plate 17 and output plate 21.

The group of input universal joints 18'', 19'' and 20'' in robotic manipulators 10 and 10' could alternatively be replaced by a group of three two axes gimbals as could the group of output universal joints 18''', 19''' and 20'''. Rather than showing such substitutions, a further robotic manipulator, 10'', shown in the perspective view of FIG. 16, has a composite extension plate, 50, provided beyond output plate 21 with respect to base plate 12 supporting a yoke arrangement, 51. Extension plate 50 has therein a group of three gimbals, 52, 53 and 54, such that plate 50 is threadedly engaged through those gimbals by, and so supported by, output shafts 22, 23 and 24 extending from plate 21. Extension plate 50, so arranged, provides an outer output operating surface that can reach a greater angular range with respect to base plate 12 than can the outer surface of output plate 21. Parts in robotic manipulator 10'' similar to those in robotic manipulator 10 have the same designators in each of their respective drawings. Differing portions of robotic manipulator 10'' are shown in these two figures, and the motors and drive trains for this manipulator, identical or similar to those for robotic manipulator 10, have been omitted in them.

Figure 17:
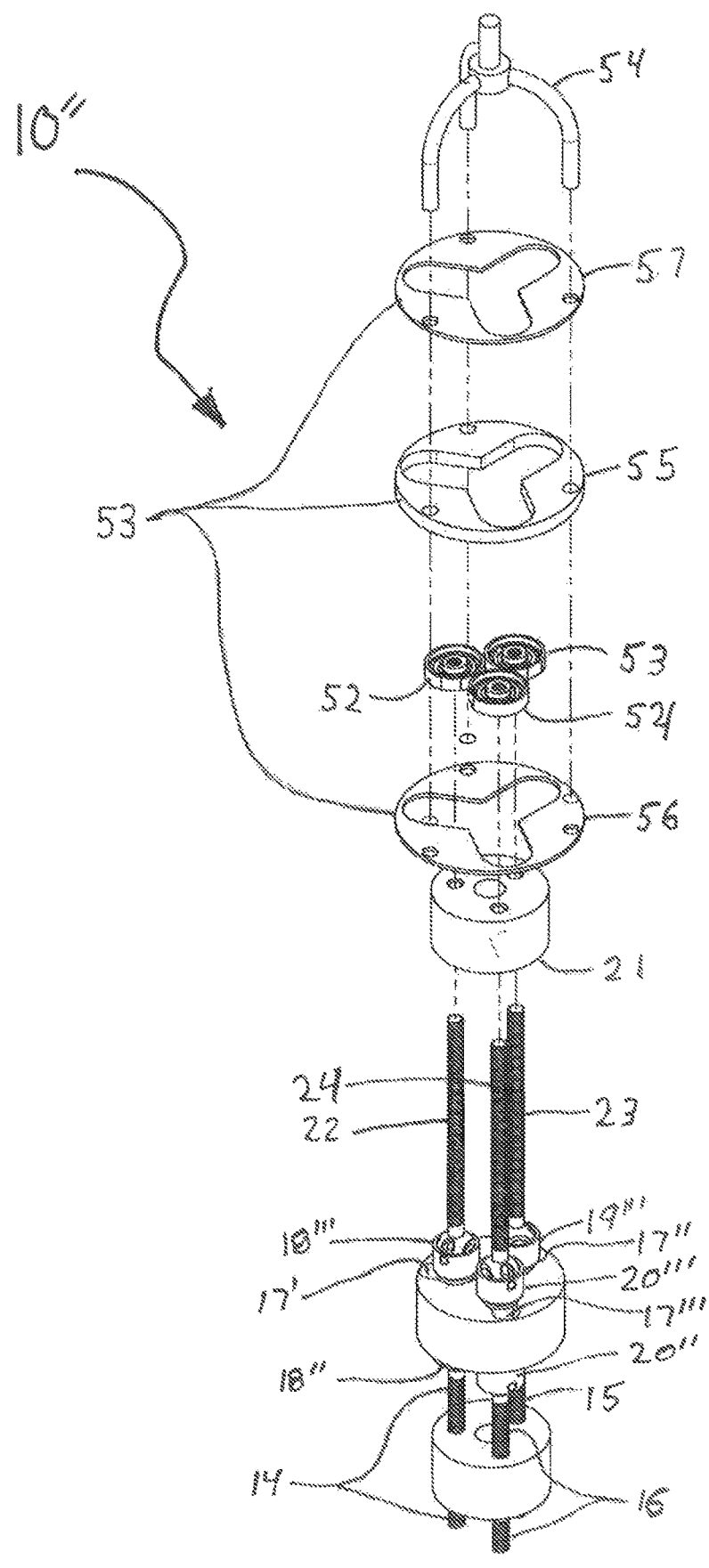
FIGS. 17 and 18 show an exploded view of a portion of the embodiment portion shown in FIG. 16 and a perspective view of a part shown in FIGS. 16 and 17.

FIG. 17 shows an exploded view of extension plate 50, yoke 51 and gimbals 52, 53 and 54 positioned above output plate 21 which is shown in turn above output shafts 22, 23 and 24. Gimbals 52, 53 and 54 each have two substantially semicircular outer edge portions across from one another which edge portions are separated from one another by two flat outer edge portions between the ends thereof that are also across from one another. These gimbals are positioned in capture slots in extension plate 50, with the flat outer edge portions of each gimbal being captured in a pair of corresponding capture channels in which the gimbal can slide. Each capture channel in a pair is across from the other in extending along the opposite sides of a corresponding capture slot.

Figure 18:
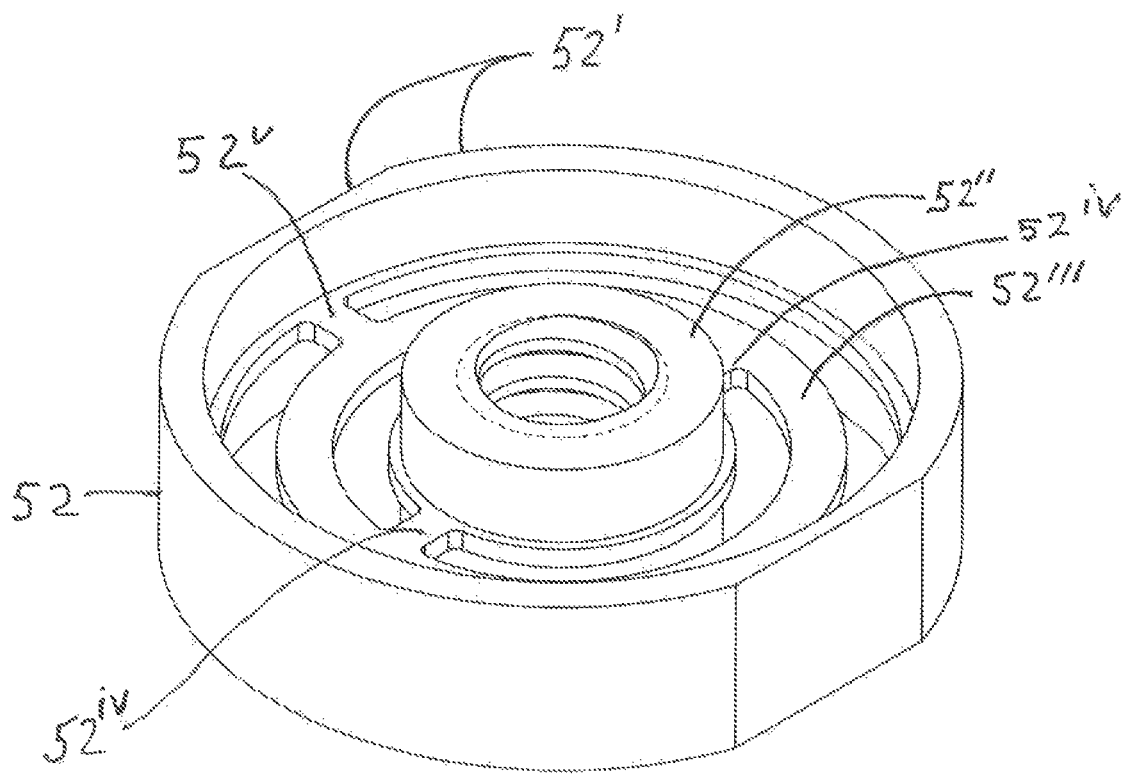

Gimbals 52, 53 and 54 are shaped commonly and so gimbal 52, as an example of each, will be described in connection with the perspective view thereof shown in FIG. 18. These gimbals each have an outer ring cylindrical shell containing the above indicated substantially semicircular and flat outer edge portions designated 52' in the example of FIG. 18. These gimbals also have a concentric circular inner ring cylindrical shell, designated 52'' in the example of FIG. 18, interior to outer ring 52' with a threaded interior shell surface for engaging the output shafts. These inner and outer cylindrical shell rings are joined to one another at the half way points of their cylindrical lengths by a concentric plate ring, 52''', positioned intermediately between them having joining bars extending therefrom. Extending from plate ring 52''' are a pair of inner bars, $52^{iv}$, each joined to inner ring cylindrical shell 52'' each on a side opposite to that of the other and along a common diameter of that shell. A pair of outer bars, $52^{v}$ (only one of which is visible in FIG. 18), extending from plate ring 52''' are joined to outer ring cylindrical shell 52' each on a side opposite to that of the other and along a common diameter that is perpendicular to the common diameter of inner bars $52^{iv}$. Gimbal 52 is formed of a resilient material so that inner bars $52^{iv}$ can be twisted to allow inner ring cylindrical shell 52'' to be rotated about the common diameter of those bars with respect to outer ring cylindrical shell 52', and so that outer bars $52^{v}$ can be twisted to allow inner ring cylindrical shell 52'' to be rotated about the common diameter of those bars, or to be rotated to an extent about both of these common diameters with respect to outer ring cylindrical shell 52'.

Extension plate 50 is seen in FIG. 17 to comprise a gimbal accommodation plate, 55, and a pair of capture plates, 56 and 57, positioned on either side of plate 55. Accommodation plate 55 and capture plates 56 and 57 each have a trinal parts opening through the thickness thereof with each trinal parts opening comprising three plate slot openings that extend from a plate central opening radially out toward the plate periphery at equal angles from one another, the end of each slot opening near the plate periphery having a semicircular edge. The larger separation difference between the parallel sides of the slot openings in accommodation plate 55 and the smaller separation difference between the parallel sides of the corresponding slot openings in each of capture plates 56 and 57 thereby form capture channels one along each side of each capture slot in extension plate 50. That is, these capture channels are located between those portions of these capture plates extending over the slot opening in accommodation plate 55 that results from the centers of the plate slots in all three plates along the slot lengths thereof being in a common plane, perpendicular to the plate surfaces about each plate slot, to thus form the capture slots. The joining together of plate 50 and capture plates 56 and 57 in this configuration, with these latter two plates being on either side of plate 55, together form composite extension plate 50. Prior to joining these plates so, a one of gimbals 52, 53 and 54 is positioned in what will be the capture channels on each side of a corresponding capture slot.

Figure 16:
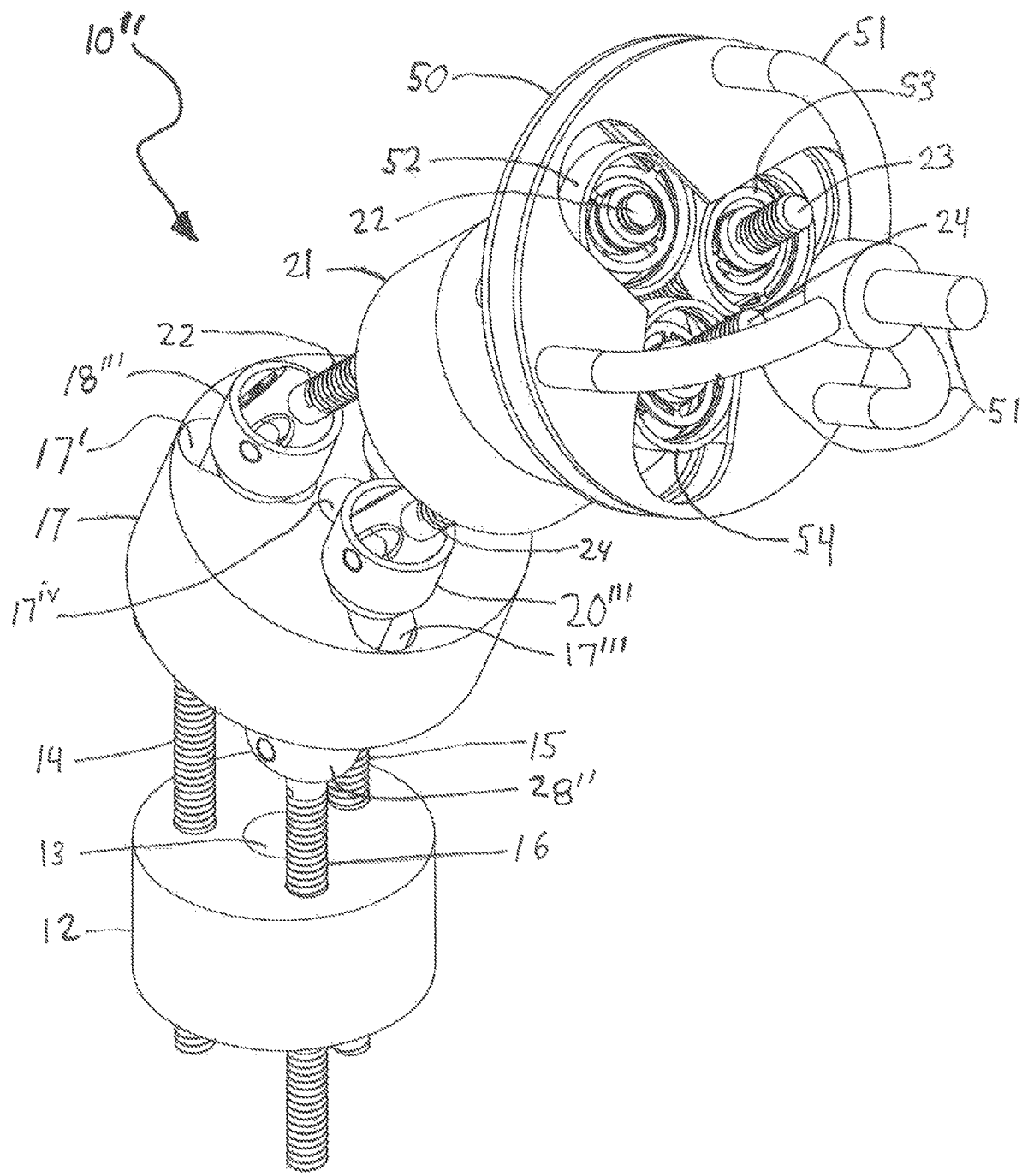
FIG. 16 shows a perspective view of another embodiment of the present invention.

As seen in FIG. 16, support yoke 51 is mounted on the outer output operating surface of extension plate 50. Yoke 51 has three curved end bars equally spaced from one another at their straight ends near the periphery of extension plate 50. These yoke bars extend outwardly from this extension outer surface to being curved toward one another so as to all meet spaced from, and over, the center of this outer surface where they are joined together by outward extending support column which they support there.

Selectively rotating the output shafts of motors 30, 31 and 32 causes rotations of output shafts 22, 23 and 24 as described above. These output shafts rotating forces the corresponding one of gimbals 52, 53 and 54 to move away from output plate 21 for one direction of shaft rotation or, alternatively, toward output plate 21 for the other direction of rotation, the inner ring cylindrical shells of these gimbals rotating (twisting) about the inner and outer bars thereof to allow the outer surface of extension plate 50 to correspondingly reorient. The use of just one group of three gimbals allows a maximum angular deviation of plate 50 that is only approximately half that of output plate 21 with its use of connected pairs of universal joints to form a group of three input universal joints and a group of three output universal joints.

Figure 19:
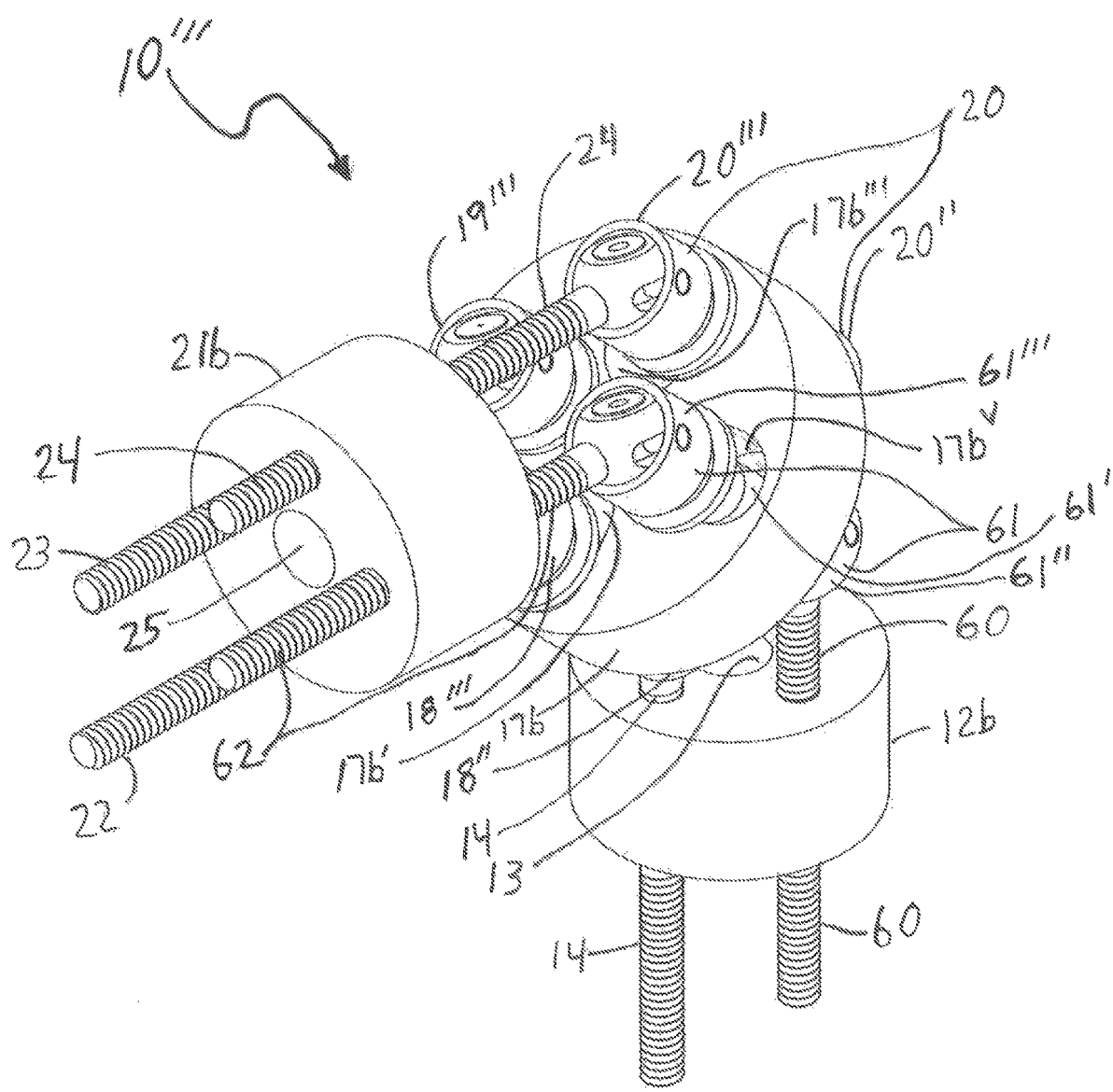
FIG. 19 shows a perspective view of another embodiment of the present invention.

The magnitude of force that can be applied to output plate 21, or its torque about a selected axis, can be increased by providing a fourth forcing shaft threadedly engaged therewith that is selectively rotatable by a fourth motor with a fourth drive train connected thereto similar to the previously described ones but which are not seen in the perspective view of FIG. 19 showing such an arrangement in a further robotic manipulator, $10'''$. Parts in robotic manipulator $10'''$ similar to those in robotic manipulator 10 have the same designators in each of their respective drawings. A differing portion of robotic manipulator $10'''$ is shown in this figure, and the motors and drive trains for this manipulator, identical or similar to those for robotic manipulator 10, have been omitted in it. The remaining part of that robotic manipulator is shown in that figure beginning with a fourth input shaft, 60, threadedly engaged with a four threaded hole base plate, 12b, and connected to the fourth drive train. A fourth radially extending slot, $17b^v$, extends through a coupling plate 17b as do each of three other slots, $17b'$, $17b''$ and $17b'''$, (in and about which are provided coupled universal joint pair assemblies 18, 19 and 20, respectively). These four slots are each through plate 17b so as to be positioned 90° from the two neighboring slots on either side thereof. A fourth coupled universal joint pair assembly, 61, is slidably positioned in and about slot $17b^v$ with this slot having a threaded coupling shaft, 61', of this assembly extending therethrough. Shaft 61' is connected on one end thereof to an input universal joint, 61'', on the base plate 12b side of plate 17b and which joint in turn is connected to fourth input shaft 60. Shaft 61' is also connected on the other end thereof to an output universal joint, 61''', which is on the other side of plate 17b on which side there is provided a four threaded hole output plate 21b. There, output universal joint 61''' is connected to a fourth output shaft, 62, threadedly engaged with plate 21b.

Fourth input shaft 60, fourth coupled universal joint pair assembly 61, and fourth output shaft 62 are all similar to their counterparts described above, and the connections between them are similar to the connections between those counterparts again as described above. Coupling plate 17b differs from coupling plate 17 in having an additional slot $17b^v$, but also in having all of the slots therein wider than the slots in plate 17 to thereby allow for lateral sliding movement of the coupled universal joint pair assemblies therein in addition to radial sliding movements of them.

In many uses of robotic manipulators, some sort of output tool or other kind of operating device will need to be mounted on the robotic manipulator output plate outer surface to provide there some desired operating capabilities, controlled from a location behind the base plate, once the robotic manipulator has, from such a control location, positioned the output plate at an operating location pertinent to the desired operations. Among the possibilities for doing so is to add a rotatable operations shaft at the outer surface of the output plate to provide selected rotary mechanical motion there which can used as desired through being selectively rotated from a control location somewhere behind the base plate.

Figure 20:
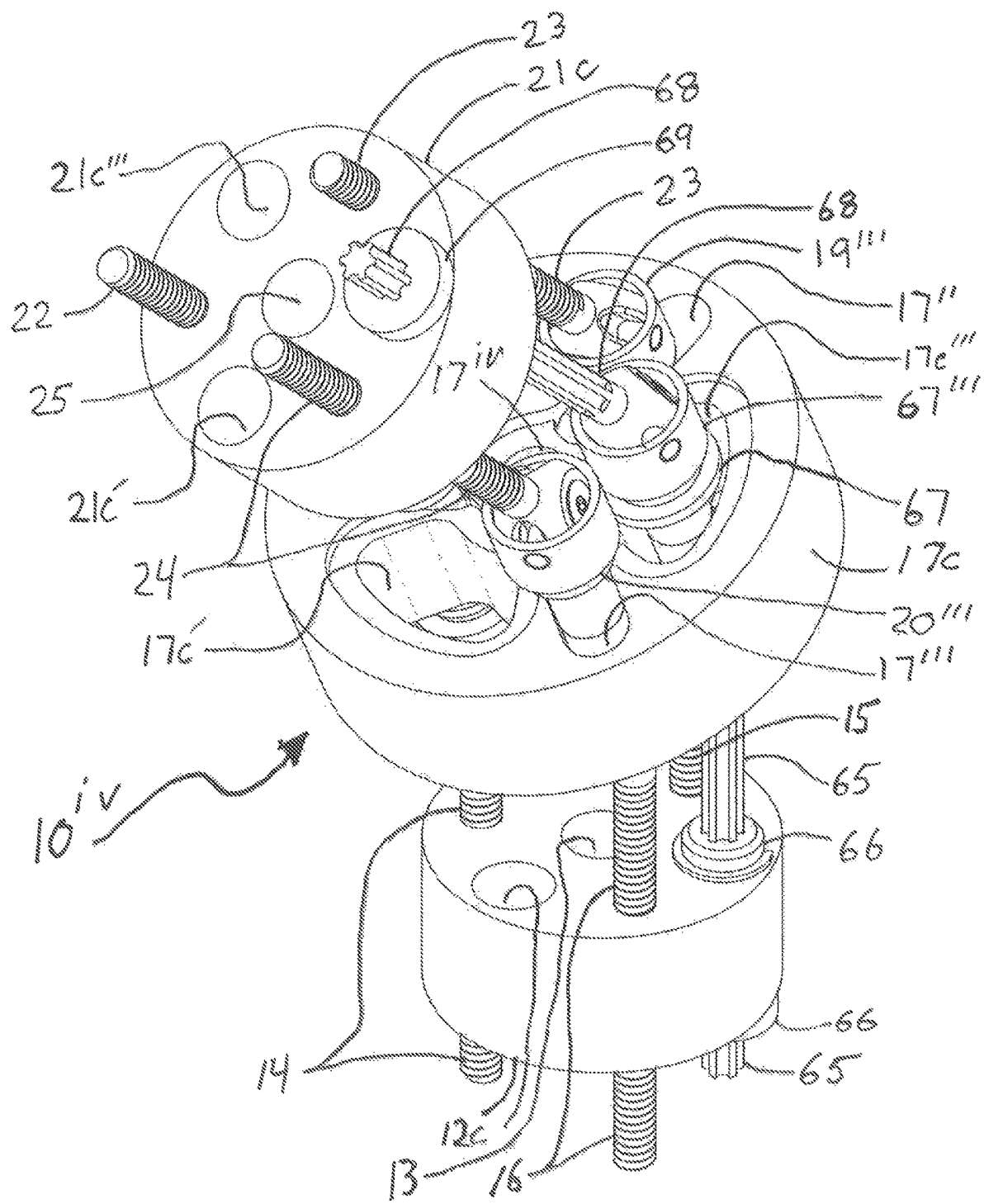
FIG. 20 shows a perspective view of another embodiment of the present invention.

One arrangement for doing so for robotic manipulator 10 of FIG. 1 is shown in the perspective view of FIG. 20 of a further robotic manipulator, $10^{iv}$. Parts in robotic manipulator $10^{iv}$ similar to those in robotic manipulator 10 have the same designators in each of their respective drawings. Differing portions of robotic manipulator $10^{iv}$ are shown in this figure, and the motors and drive trains for this manipulator, identical or similar to those for robotic manipulator 10, have been omitted in them. Robotic manipulator $10^{iv}$ has provided therein three modified plates, base plate 12c with circular openings 12c', 12c'' (not seen) and 12c''' (filled by a bushing and shaft) therethrough, coupling plate 17c with circular arc slots 17c', 17c'' (not seen) and 17c''' therethrough each between otherwise adjacent pairs of slots 17', 17'' and 17''', and output plate 21c with circular openings 21c', 21c'' and 21c''' (filled by a bushing and shaft) therethrough.

Each circular arc opening in coupling plate 17c has two opposite sides each following a circular arc with different radii with each pair of adjacent arc ends joined together by fillets therefrom to a side substantially following an extended radius of plate center opening $17^{iv}$ to thereby form the two remaining sides. There is, at each end of each circular arc opening, a bordering recess from the corresponding surface of plate 17c that follows each opening side to form a continual recess strip along those sides. If each of the input shafts 14, 15 and 16 were along a straight line axis with their corresponding one of output shafts 22, 23 and 24 so that plates 12c, 17c and 21c were all parallel to one another, much like the position arrangement shown in FIG. 3, an axis joining the centers of a circular opening in base plate 12c and a corresponding circular opening in output plate 21c would also pass through a center of a corresponding circular arc opening in coupling plate 17c.

As indicated, what would be a circular opening 12c''' has a splined input shaft, 65, extending through a splined collared bushing, 66, rotatably mounted in that opening. Bushing 66 has a larger diameter collar positioned against the motors side of plate 12c, and a smaller diameter collar facing coupling plate 17c that fits through circular opening 12c''' but is prevented from going into that opening by a snap ring between this smaller collar and the coupling plate side of plate 12c. Splined input shaft 65 extends from bushing 66 to a further coupled universal joint pair assembly, 67, that is slidably positioned in and about circular arc slot 17c''' with this slot having a threaded coupling shaft, 67', of this assembly extending therethrough. Shaft 67' is connected on one end thereof to an input universal joint, 67'', (not seen) on the base plate 12c side of plate 17c where its collar can slide in the border recess about circular arc slot 17c'''. The other side of input universal joint 67'' is in turn connected to fourth input shaft 65. Shaft 67' is also connected on the other end thereof to an output universal joint, 67''', which is on the other side of plate 17c facing output plate 21c where its collar can slide in the border recess on that side about circular arc slot 17c'''. Output universal joint 67''' is connected on this other side to output plate 21c by an output shaft, 68, extending from this joint to a further splined collared bushing, 69, like bushing 66, that is rotatably mounted in what would otherwise be circular opening 21c'' in output plate 21c with its snap ring side facing coupling plate 17c.

The addition of another motor and drive train to input shaft 65 behind base plate 12*c*, which can be similar to those provided for the input shafts, and selectively rotating its output shaft, allows selective rotation of output shaft 68 at the outer surface of plate 21*c*. The exposed portion there of output shaft 68 can serve as a power takeoff source or controlled rotary motion source for operating further devices provided at that surface. An example of doing so is shown in the perspective view of FIG. 21 and the cross section view of FIG. 22 for a modified robotic manipulator, 10$a^{iv}$, in having a clamping or gripping or cutting capability operating device being added at this outer surface to be controlled there in part by supplying controlled rotary motion from output shaft 68. Parts in robotic manipulator 10$a^{iv}$ similar to those in robotic manipulator 10 have the same designators in each of their respective drawings. Differing portions of robotic manipulator 10$a^{iv}$ are shown in these two figures, and the motors and drive trains for this manipulator, identical or similar to those for robotic manipulator 10, have been omitted in them.

A support stand, 70, in the form of a vertical stand plate having at one end two support stems each extending from the stand plate body to be on one of the opposite sides of an accommodation recess opening, 71, extending from the plate end inward. Stand 70 is mounted on the outer surface of plate 21*c* by affixing each of those two support stems to that surface so as to position the stand plate of stand 70 over the center of, and on opposite sides of, interior opening 25 provided through output plate 21. The other end of support stand 70 is formed as a shackle having a pair of arms spaced apart by an operation recess space with these arms extending from the plate body to be on one of the opposite sides of the operation recess space opening which opening extends inward from this other plate end. Each arm has a pivot opening near its end farthest from the stand plate body and through each of which a pivot pin extends which also extends through the closer rotation pivot openings in an outer closer, 72, and an inner closer, 73, positioned between these arms.

Outer closer 72 is substantially L-shaped having an oblong base plate, 72', extending from two joining portions of the closer that together extend along a common axis at which portions this base plate is joined to an oblong closing plate, 72", extending at an angle from these joining portions. The closer rotation pivot openings in outer closer 72 each extend through one of these joining portions along their common axis which axis is perpendicular to the lengths of base plate 72' and closing plate 72". An operation pivot opening is provided through base plate 72' at the end thereof farthest from the joining portions and extending parallel to the closer rotation pivot openings. In addition, a coupling slot is provided in outer closer 72 extending between and through the joint portions thereof across the common axis and then extending from there a distance into base plate 72' along its length and a distance into closing plate 72" along its length. Also, there is a cup-like recess in closing plate 72" just past the end of the coupling slot portion therein extending inward from the plate surface thereof making the smallest angle with base plate 72'.

Inner closer 73 is also substantially L-shaped having an oblong base plate, 73', extending from a joining portion of this closer at which portion this base plate is joined to an oblong closing plate, 73", extending at an angle from this joining portion. The joining portion of this closer has a closer rotation pivot opening therethrough extending perpendicular to the lengths of base plate 73' and closing plate 73", and is narrow enough to allow it to be positioned in the coupling slot of outer closer 72 so that its closer rotation pivot opening is also along the common axis of the two joining portions of this outer closer. Closing plate 73" can be wider than the coupling slot of outer closer 72 for better gripping capabilities or could have a very narrow edge facing outer closer base plate 72' for better cutting capabilities (as can be closing plate 72"). An operation pivot opening is provided through closer base plate 73' at the end thereof farthest from the joining portion, and extending parallel to the closer rotation pivot opening. Here too, a cup-like recess in closing plate 73" is provided just past the end of the joining portion thereof extending inward from the plate surface thereof making the smallest angle with base plate 73'.

The pivot pin in the pivot openings of the arms of support stand 70 extends through the closer rotation pivot openings in the joining portions of outer closer 72 and inner closer 73 so that these joining portion are positioned in the operation recess space of that stand, and so these closers can then be rotated in that space for selected operations of the device. There are two operation control and implementation arrangements for the operating device provided at the outer surface of plate 21*c* in FIGS. 21 and 22. The first of these is a device orientation control based on selective operations of the exposed portion there of splined output shaft 68 fitted into the interiorly splined end of a rotaty-to-linear motion converter, 74. Converter 74 is provided as a cylindrical shell having a threaded interior at one end of the opening through the length thereof that is threadedly engaged in these converter interior threads with a threaded end of an actuation shaft, 75, and a splined interior at the other end of that opening engaged with shaft 68. Rotation of shaft 68 in one direction or the other rotated the cylindrical shell of converter 74 to thereby cause actuation shaft 75 to extend or retract with respect to the threaded end of that shell.

The end of actuation shaft 75 opposite the threaded end of that shaft has an operation pivot opening therethrough with a pivot pin extending through it and through operation pivot openings in the arms on either side of that shaft positioned in the recess space between these arms, these arms belonging to the first shackle at a first end of a double shackle link, 76. A second shackle at the opposite end of link 76 has the end of closer base plate 73' farthest from its joining portion positioned in the recess space between its arms, these arms also having operation pivot openings in each of them with a pivot pin extending through them and through the operation pivot opening provided through closer base plate 73' at that end thereof. Thus, selective rotations of splined shaft 68 by the corresponding connected motor to thereby force the shackled end of actuation shaft 75 toward and away from the converter cylindrical shell allows selecting over an angular range the angle of closing plate 73" of interior closer 73 with respect to the outer surface of output plate 21*c* by rotating that closer in either direction about the rotation pivot pin through it and stand 70.

Outer closer 72 can also be rotated in either direction about the rotation pivot pin through it and stand 70 (and also through interior closer 73) by a shackle end pull cable, 77. Cable 77 extends from some control position behind base plate 12*c* through interior opening 13, through interior opening 17$^1v$ of coupling plate 17*c*, and through interior opening 25 of output plate 21*c* and accommodation recess opening 71 to be affixed in the joining region between two arms of a cable shackle. These two arms on either side of a recess space each have an operation pivot opening extending through them and through operation pivot opening provided in the end of base plate 72' positioned in that recess space.

Thus, selective pullings on shackle end pull cable 77 from the control position behind base plate 12c selectively forces closing plate 72" against closing plate 73" at whatever angular position has been selected for closing plate 73" by the selective rotations of shaft 68. In the arrangement show in FIGS. 21 and 22, terminating a pulling on cable 77 will result in separating closing plate 72" and closing plate 73" because of a compression spring, 78, being provided between them with its ends positioned in the corresponding one of the cup-like recesses in each of these plates. One alternative could be to eliminate this spring and use, in place of the cable part of shackle end pull cable 77, a sufficiently stiff wire to force both the opening and the closing of closing plate 72" and closing plate 73".

Figure 21:
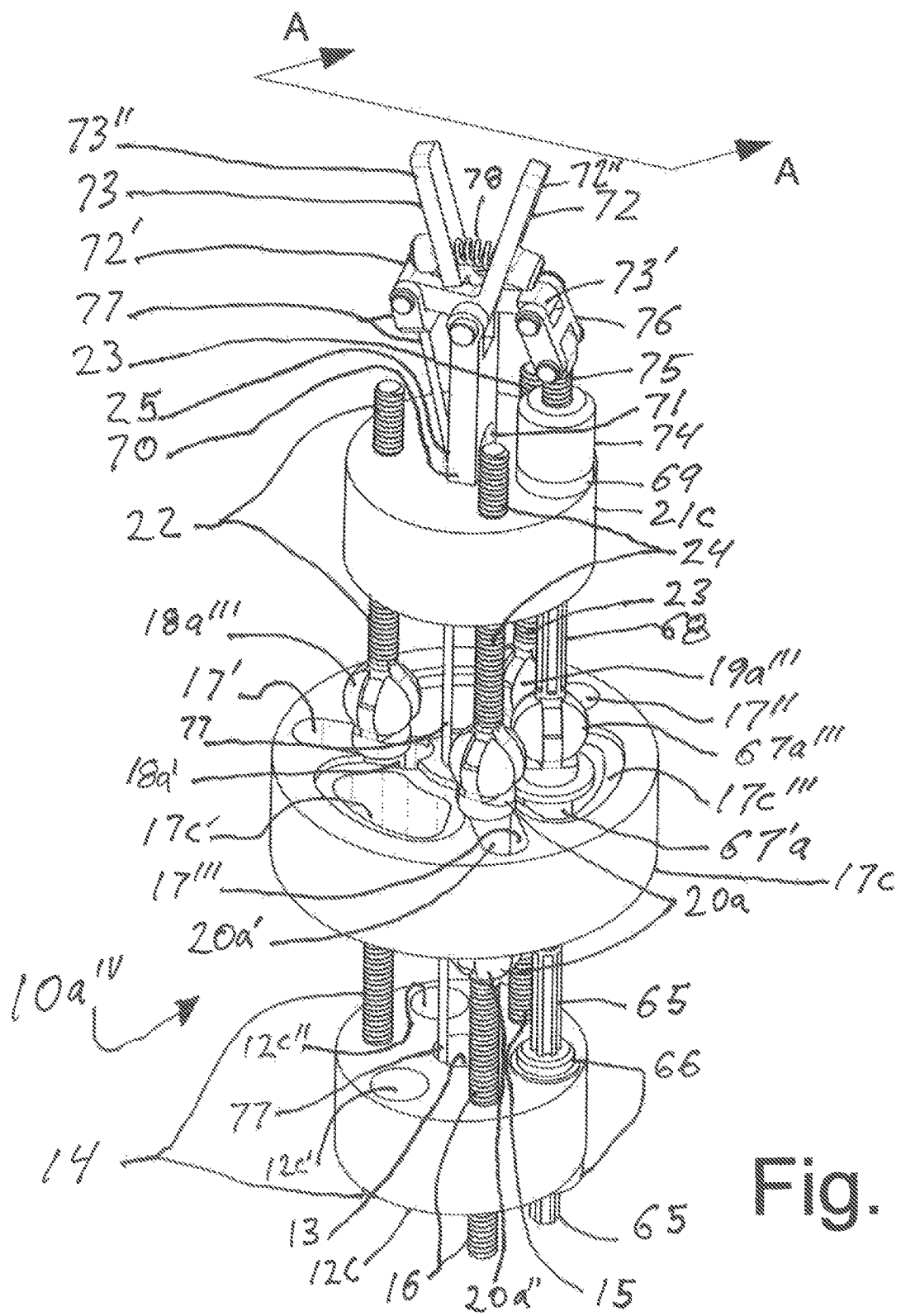
FIG. 21 shows a perspective view of another embodiment of the present invention.
Figure 22:
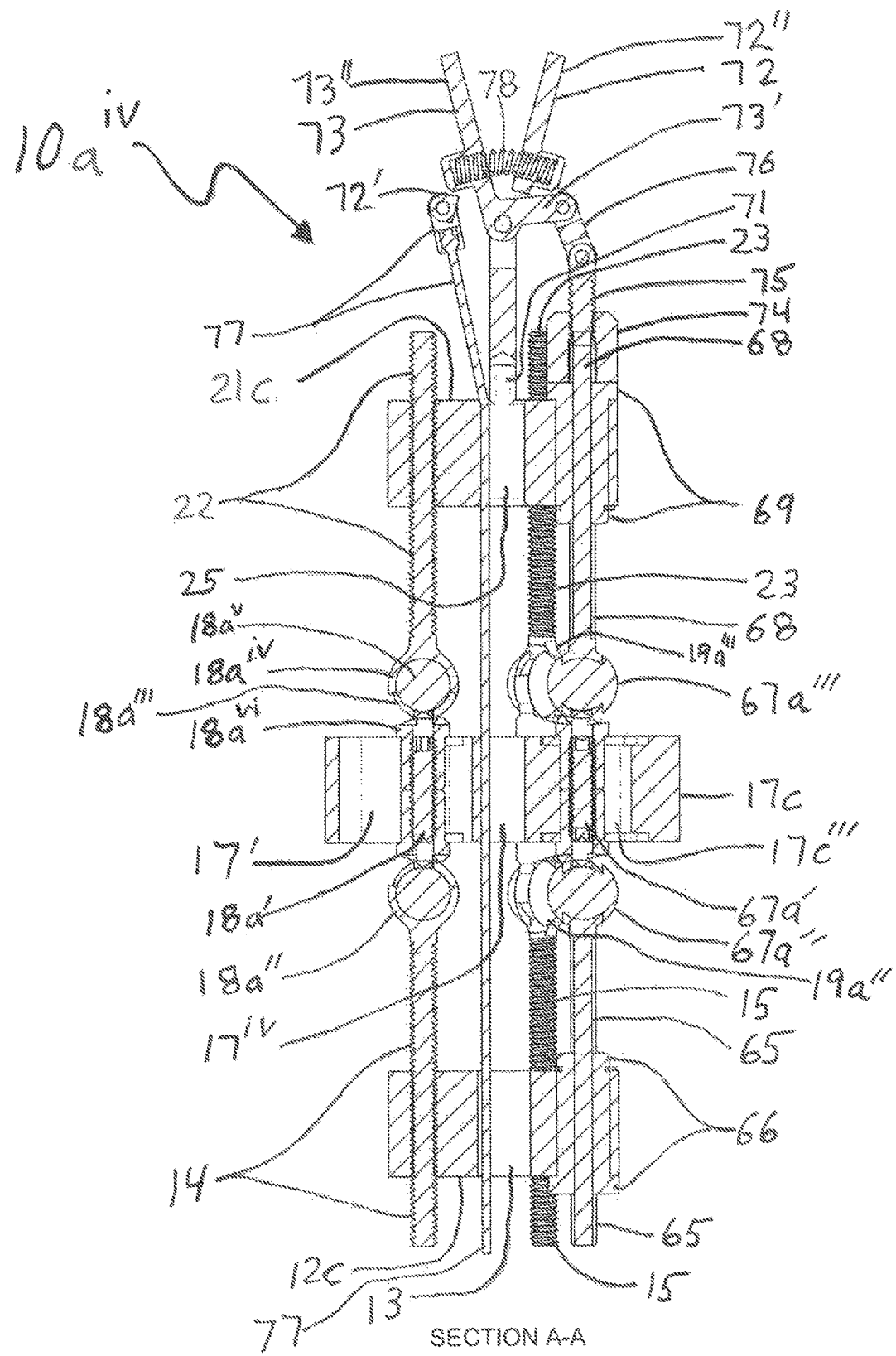
FIG. 22 shows a cross section view of the embodiment shown in FIG. 21.

Modified robotic manipulator $10a^{iv}$ of FIGS. 21 and 22 has a further difference from robotic manipulator $10^{iv}$ of FIG. 20 in that the common joint type universal joint pairs 18" and 18''', 19" and 19''', and 20" and 20''' have had substituted for them common joint type universal joint pairs $18a$" and $18a$''', $19a$" and $19a$''', and $20a$" and $20a$''' in which each of these latter universal joints is of a different type, and so of different structure, than the previous corresponding universal joint it substitutes for but which behave similarly in response to applied forces. Other kinds of universal joints with similar capabilities could also be substituted, for example, the common universal joints having the two shackles provided with rotational pivot openings in each of the arms with the arms coupled together by a cross structure, or spider, with the arm ends each in a corresponding one of the arm rotational pivot openings.

Figure 23:
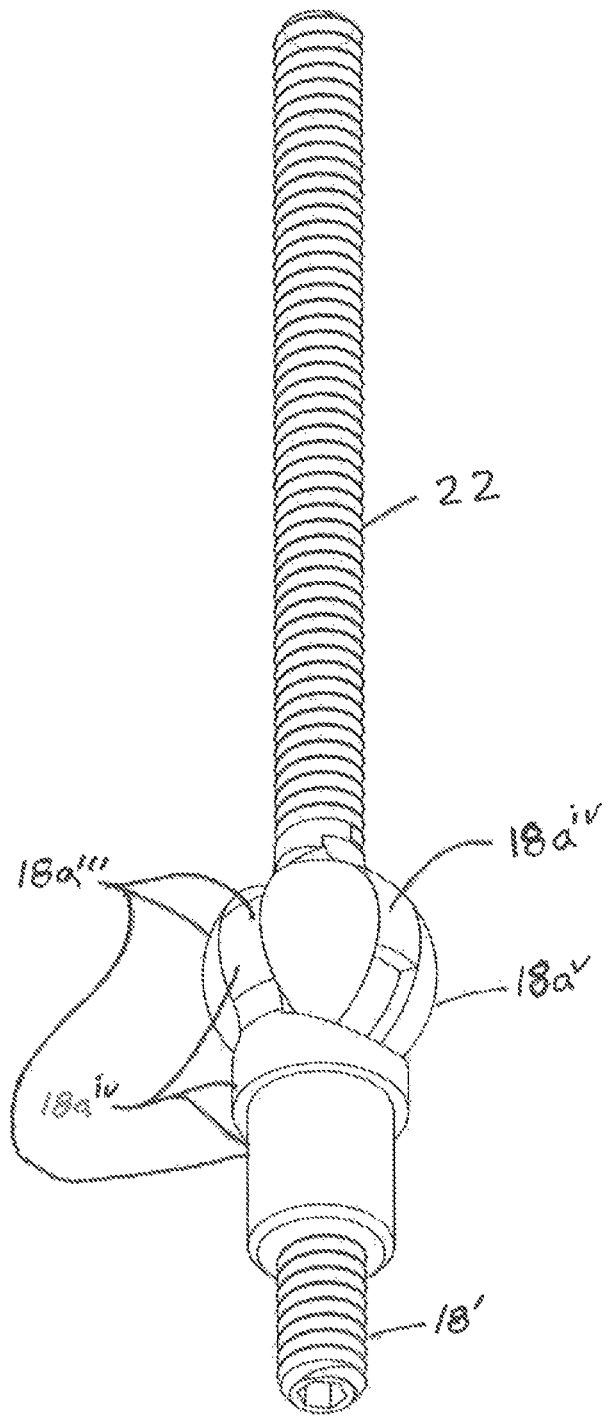
FIG. 23 shows an elevation view of a portion of the embodiment shown in FIG. 21.
Figure 24:
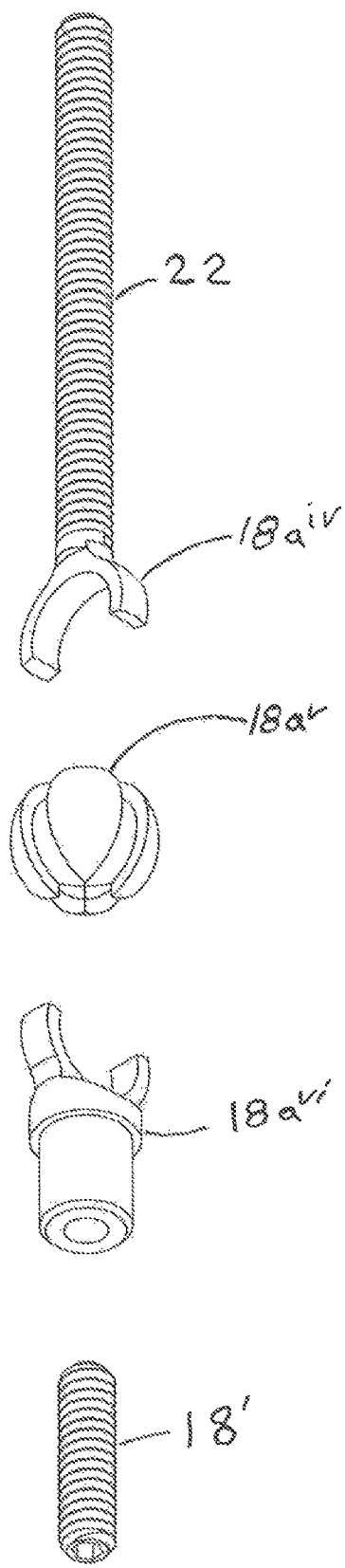
FIG. 24 shows an exploded view of the embodiment portion shown in FIG. 23.

One of the substituted universal joints shown in FIGS. 21 and 22, joint $18a$''', is shown in more detail in perspective view of FIG. 23 and the exploded perspective view of FIG. 24. Output shaft 22 is affixed to the center of a circular arc yoke, $18a^{iv}$, having two arms extending in opposite directions along a circular arc path so that they together follow a circular arc path greater than a semicircle. These arms are formed of a resilient material sufficiently resilient for their sizes to allow the ends of them to be forced a slight distance apart and then result in them returning to their circular arc positions upon removal of such a separating force. These arms are engaged in one of two channels recessed into the surface of a channeled sphere, $18a^v$, each wide enough to accept such arms therein so that the yoke can rotate about the center of the sphere in its channel, and each channel extending entirely around sphere $18a^v$ following a circular path in a corresponding plane through the sphere with the planes for each channel separated by right angles. The arms of circular arc yoke $18a^{iv}$ are initially separated by being forced into the corresponding sphere channel but return to their circular arc position once the arms ends are past the corresponding equator of the sphere so as to capture the channeled sphere between them.

The remaining channel of channeled sphere $18a^v$ has in it the similar arms of the yoke provided in a transition yoke structure, $18a^{vi}$, formed of interiorly threaded cylindrical shell affixed to the center of this yoke. This second yoke again has two arms of a resilient material extending in opposite directions along a circular arc path so that they together follow a circular arc path greater than a semicircle to also capture sphere $18a^v$, and is positioned more or less across from the previous yoke so that it can also rotate about the center of the sphere in its channel. The presence of each yoke in its channel prevents the other yoke from completely rotating about the center of the sphere to follow a full circle path.

Threaded coupling shaft 18' is provided for joint $18a$''' to connect it to corresponding input universal joint $18a$" as it was previously provided for joint 18''' to connect it to the input universal joint 18" in their corresponding coupled universal joint pair assemblies. Shaft 18' threadedly engages the interior threads in the cylindrical shell in transition yoke structure $18a^{vi}$.

Figure 25:
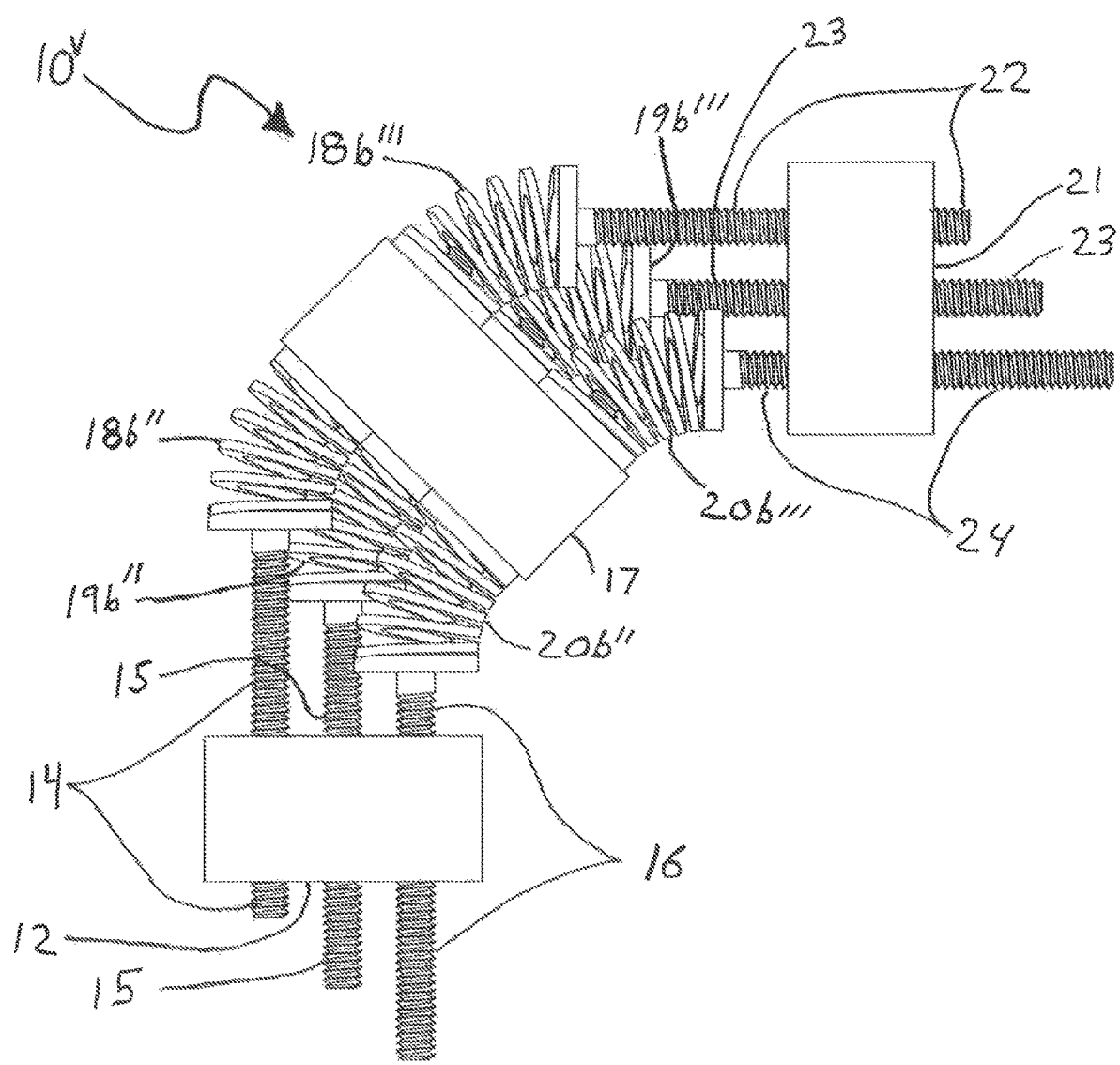
FIG. 25 shows an elevation view of another embodiment of the present invention.

Even simpler, and often cheaper, universal joint substitutions in these robotic manipulators can be used in some circumstances, perhaps some of those in which positioning of the robotic manipulator output plate could be tolerated to be less precise or less repeatable. In any event, a further substitution example is shown in elevation view of FIG. 25 of another robotic manipulator, $10^v$, in which a helical spring affixed between a pair of connection plates forms another set of input universal joints $18b$", $19b$" and $20b$", each to correspondingly be substituted for each of input universal joints 18", 19" and 20" in robotic manipulator 10 which manipulators are otherwise similar. Similarly, a helical spring affixed between a pair of connection plates forms another set of output universal joints, $18b$''', $19b$''' and $20b$''', each to correspondingly be substituted for each of output universal joints 18''', 19''' and 20''' in robotic manipulator 10 to, together, provide in robotic manipulator $10^v$ counterparts to the coupled universal joint pair assemblies of robotic manipulator 10. The input and output universal joint springs have their facing connection plates connected by a threaded shaft extending through the slots in coupling plate 17, the opposite connection plates of the input universal joint springs are each connected to a corresponding one of the input shafts, and the opposite connection plates of the output universal joints are each connected to a corresponding one of the output shafts. These helical springs can be formed from either some suitable metal or some suitable of plastic.

Figure 26:
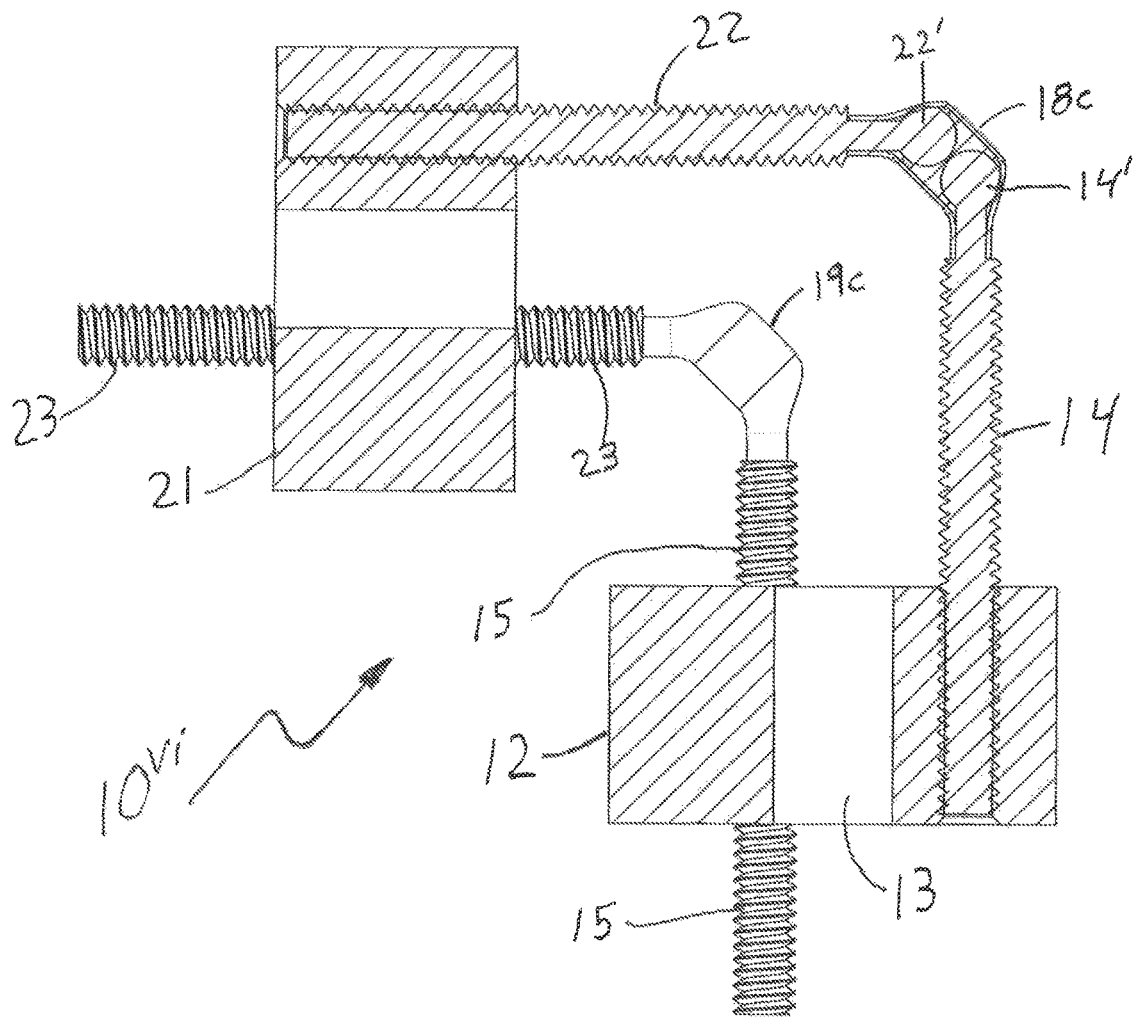
FIG. 26 shows a mixed elevation and cross section view of another embodiment of the present invention.

A significantly simpler configuration is shown as another robotic manipulator, 10', in the mixed elevation and cross section view of FIG. 26 in which coupling plate 17 and the coupled universal joint pair assemblies of robotic manipulator 10 have been eliminated by use of a set of sheath-bound double sphere joints in their place to form a further set of coupled universal joint assemblies, 18c, 19c and 20c. Input shaft 14 extending from base plate 12 has a neck extending from the end thereof supporting a sphere, 14', that is held against a sphere, 22', supported on a neck extending from output shaft 22, extending in turn from output plate 21, by an elastomeric tube in assembly 18c tightly encasing both spheres. The smaller tube interior diameter at each of its ends past the corresponding sphere tightly encases the neck there supporting that sphere so that the two spheres remain encased within the interior of the tube despite turning against each other during angular changes forced between input shaft 14 and output shaft 22 by selected rotations of the manipulator input shafts 14, 15 and 16 (not shown) caused by selected rotations of the motors connected thereto as described above. Input shaft 15, coupled universal joint assembly 19c and output shaft 23 are of a similar construction and are also capable of providing or accepting similar angular changes between those two shafts. So are input shaft 16, coupled universal joint assembly 20c and output shaft 24 though not seen in the figure because of being obstructed in that view by input shaft 15, coupled universal joint assembly 19c and output shaft 23.

Another saving in the cost of constructing robotic manipulator 10, and in the volume of space occupied by it, but at the cost of having less force available to manipulate the output plate, is achievable by eliminating one motor and the associated drive train, input shaft, and output shaft combination. Such a robotic manipulator, $10^{vii}$, is shown in the two elevation views of FIGS. 27 and 28. In addition, though not required for a two motor robotic manipulator, a rotatable operations shaft at the outer surface of the output plate to provide selected rotary mechanical motion there has been provided using the interior openings of the base and output plates and of hinged coupling arrangement between them as is to be described. Parts in robotic manipulator $10a^{iv}$ similar to those in robotic manipulator 10 have the same designators in each of their respective drawings. Differing portions of robotic manipulator $10a^{vii}$ are shown in these two figures as well as different views.

Figure 27:
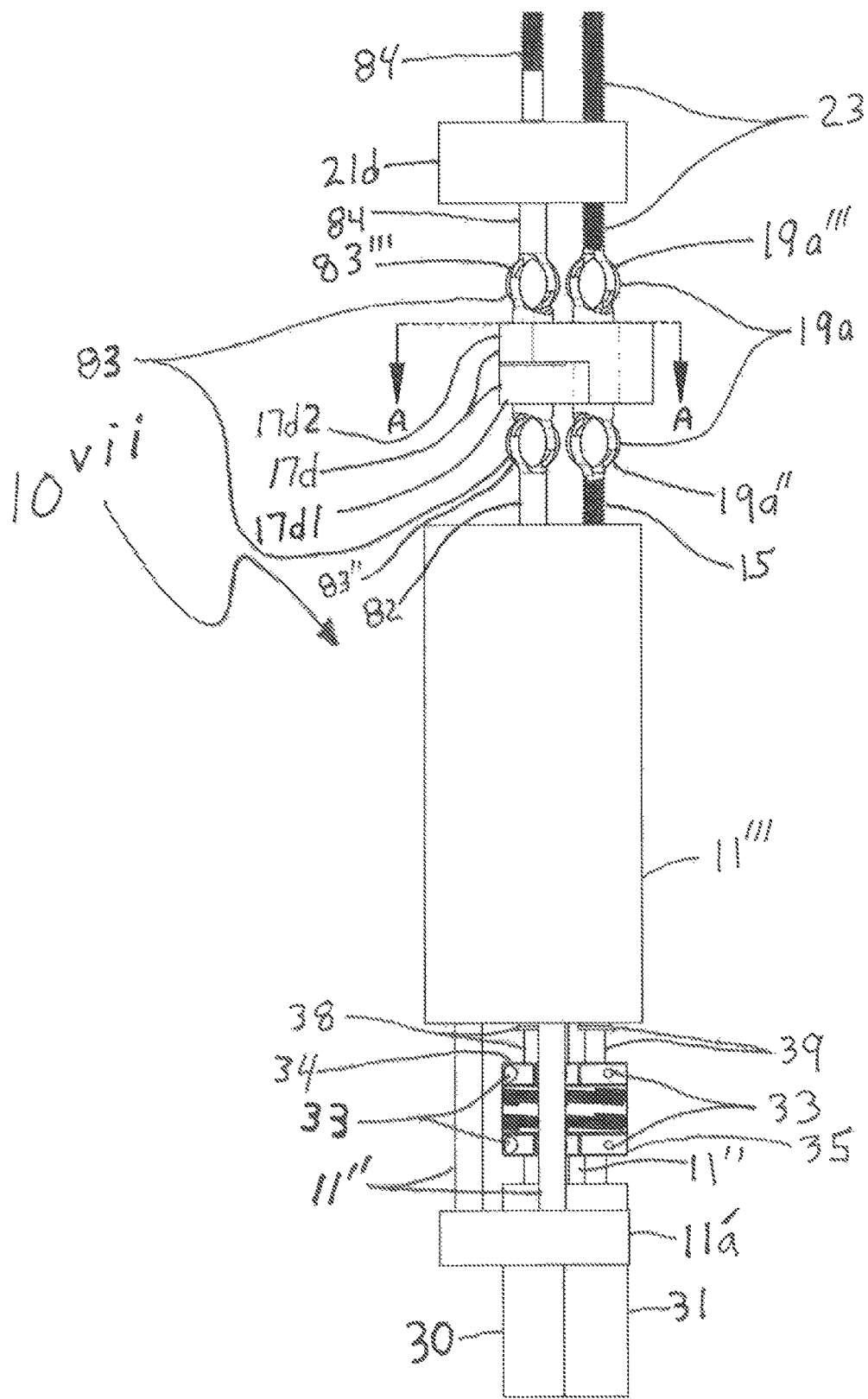
FIGS. 27 and 28 show perspective views of a further embodiment of the present invention.
Figure 28:
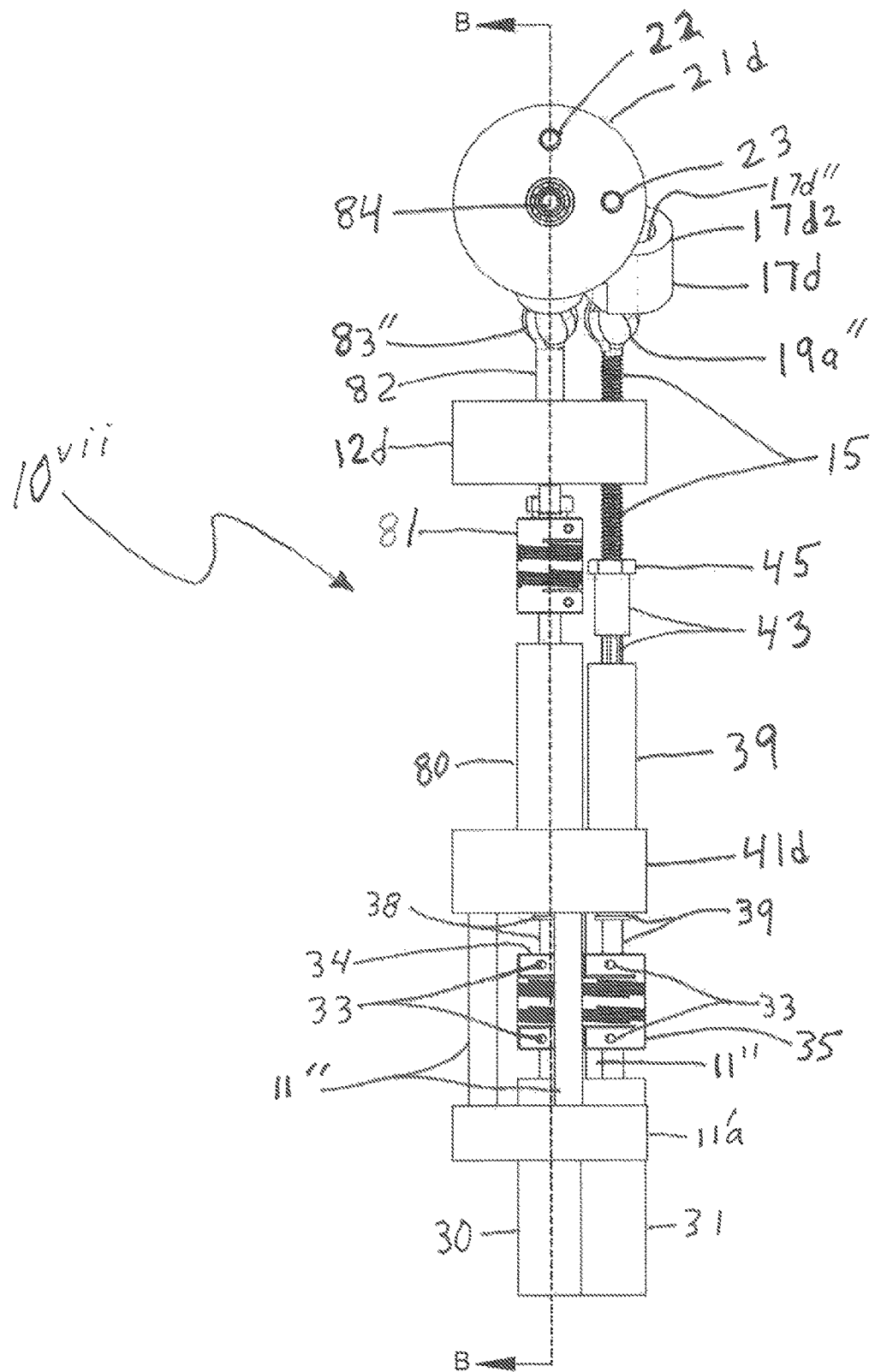

Robotic manipulator $10a^{vii}$ is shown in elevation in FIGS. 27 and 28 but with output plate 21*d* in alternative orientations in them, and, although protective cylindrical shell sleeve 11''' has been included in the manipulator in FIG. 27, this sleeve has been omitted from the manipulator in FIG. 28 to reveal more of the structure shielded thereby. Input shaft 16 and motor 32, along with the drive train connecting them, coupled universal joint pair assembly 20, and output shaft 24 have all been omitted in this manipulator. Input shafts 14 and 15 and corresponding motors 30 and 31, along with the corresponding drive trains connecting them, the corresponding coupled universal joint pair assemblies 18*a* and 19*a*, and the corresponding output shafts 22 and 23 have been repositioned to be 90° apart from one another at, or projected on, the outer surface of modified base plate 12*d* with respect to interior opening 13 therein, and similarly positioned at, or projected on, the outer surface of modified output plate 21*d* with respect to interior opening 25 therein for the orientation of the manipulator shown in FIG. 28.

Figure 29:
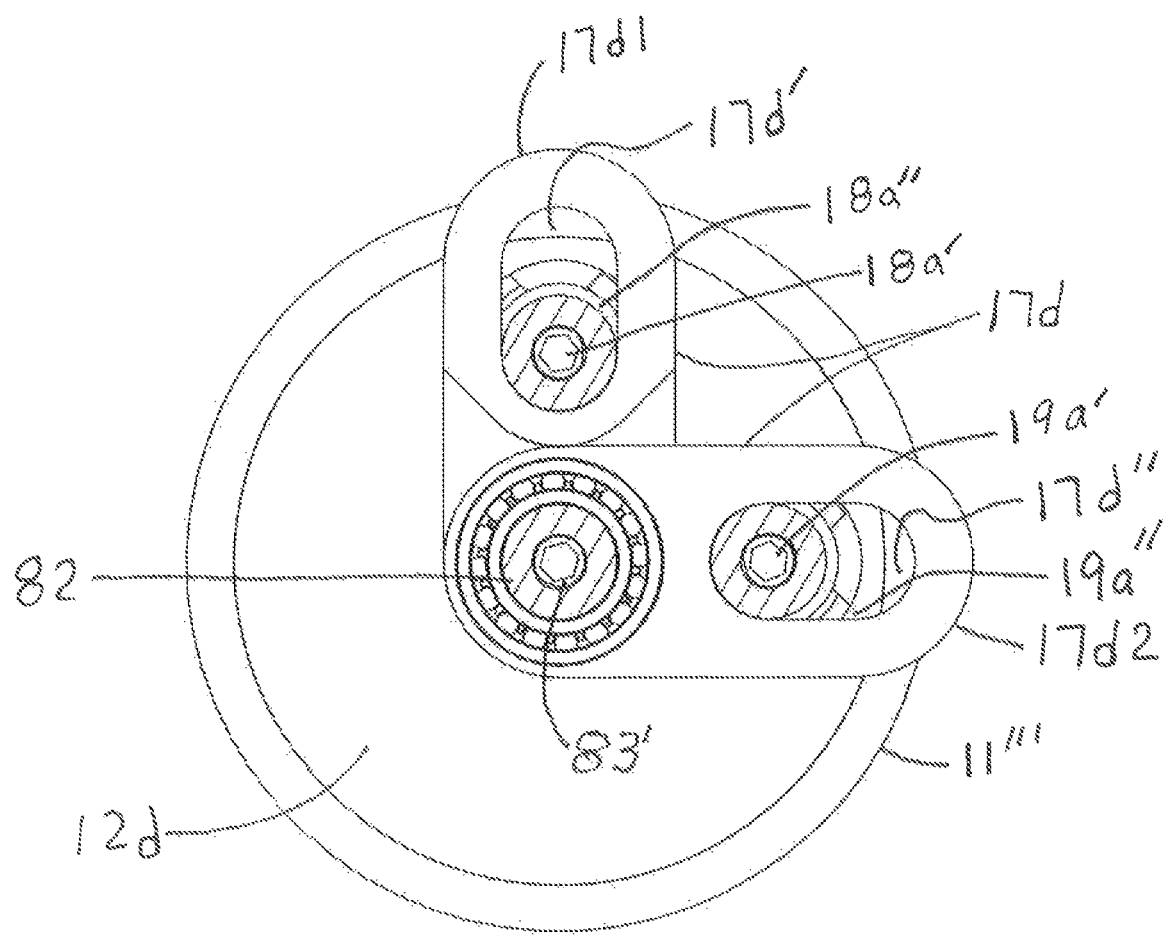
FIG. 29 shows a cross section view of the embodiment shown in FIG. 27.

Coupled universal joint pair assemblies 18*a* and 19*a*, however, are positioned in a link structure, 17*d*, in and through slots 17*d'* and 17*d''* each provided as an oblong opening along a pair of loop links, 17*d*1 and 17*d*2, respectively, provided in that structure extending through those loop links near the outer ends thereof. These assemblies are maintained in these slots by collars thereabout that are slidable over the surfaces of these slots adjacent thereto. These loop links are rotatably connected to one another in that structure about an end opening through each of their inner ends so as to have these end openings coaxially positioned with respect to one another to together form a link structure interior opening, $17d^{iv}$, extending parallel to the slot openings as seen in the cross section view of FIG. 29. Loop links 17*d*1 and 17*d*2, being capable of rotating with respect to one another, and each having one of coupled universal joint pair assemblies 18 and 19 in a corresponding one of slots 17*d'* and 17*d''* in them, allows these assemblies to move radially, and to a greater extent laterally because of loop link rotation capability in response to the forces on the assemblies resulting from selective rotations of the input shafts due to selective rotations of motors 30 and 31 connected thereto.

Figure 30:
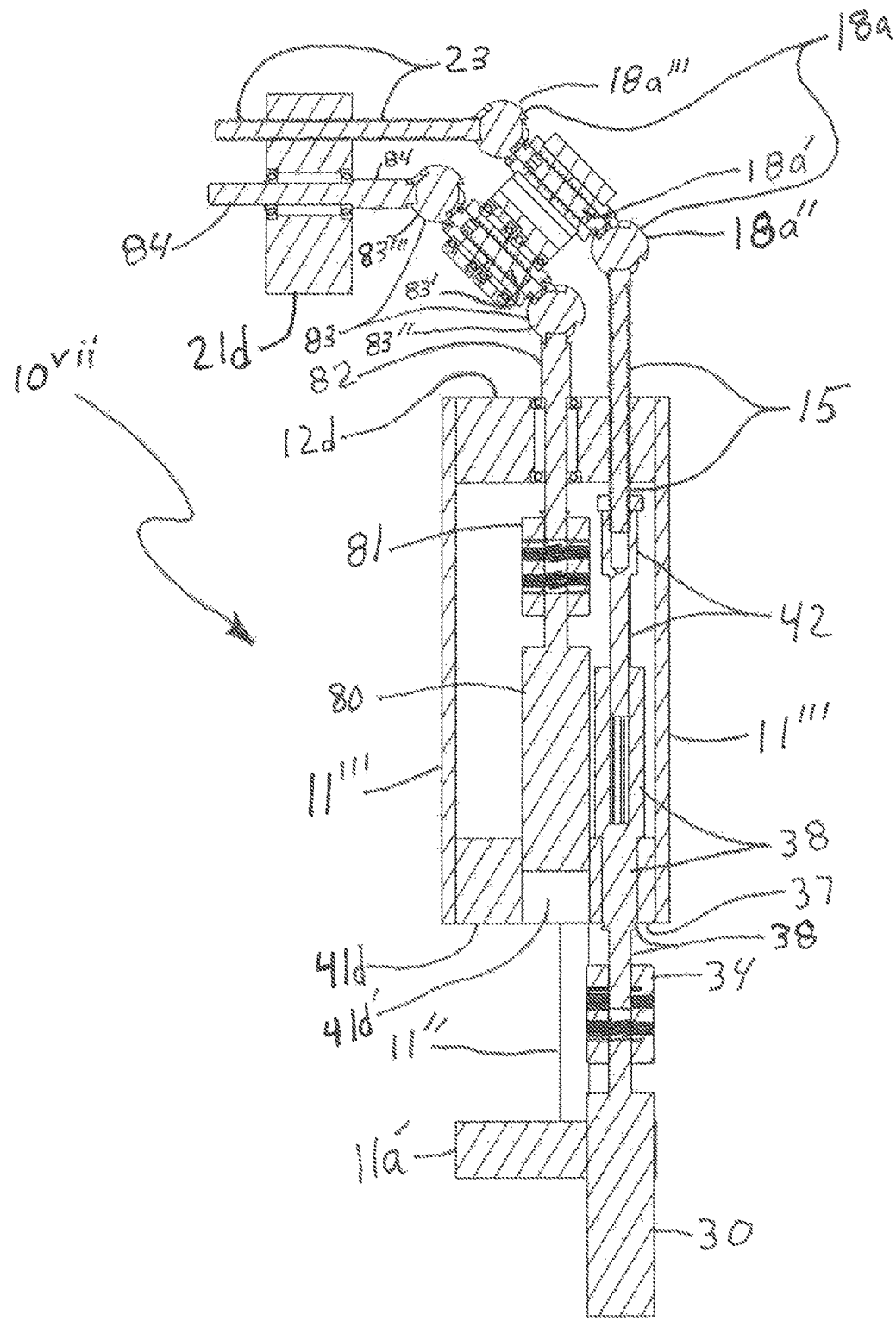
FIG. 30 shows a cross section view of the embodiment shown in FIG. 28.

As best seen in the cross section view of FIG. 30, a rotatable operations shaft is added at the outer surface of output plate 21*d* to provide selected rotary mechanical motion there which can used as desired through being selectively rotated from a motor, 80, mounted in an interior opening 41*d'* in modified bushing plate 41*d* which is modified to accommodate the drive trains connecting motors 30 and 31 to drive shafts 14 and 15, respectively. Motor 80 is connected by a beam coupler, 81, like beam couplers 34 and 35, to an input shaft, 82, supported in a bearing seated in interior opening 13 in modified base plate 12*d*. Input shaft 82 is connected to a coupled universal joint pair assembly, 83, like assemblies 18*a* and 19*a*, positioned in link structure interior opening $17d^{iv}$. Thus, coupled universal joint pair assembly 83 has a threaded shaft, 83', extending through link structure interior opening $17d^{iv}$ connecting an input universal joint, 83'', to an output universal joint, 83'''. Output universal joint 83''' is connected to an output shaft, 84, supported in a bearing seated in interior opening 25 in modified output plate 21*d*. Selective rotations of the shaft of motor 80 allow selective rotations of output shaft 84 at the outer surface of plate 21*d*. The exposed portion there of output shaft 84 can serve as a power takeoff source or controlled rotary motion source for operating further devices provided at that surface.

Figure 31:
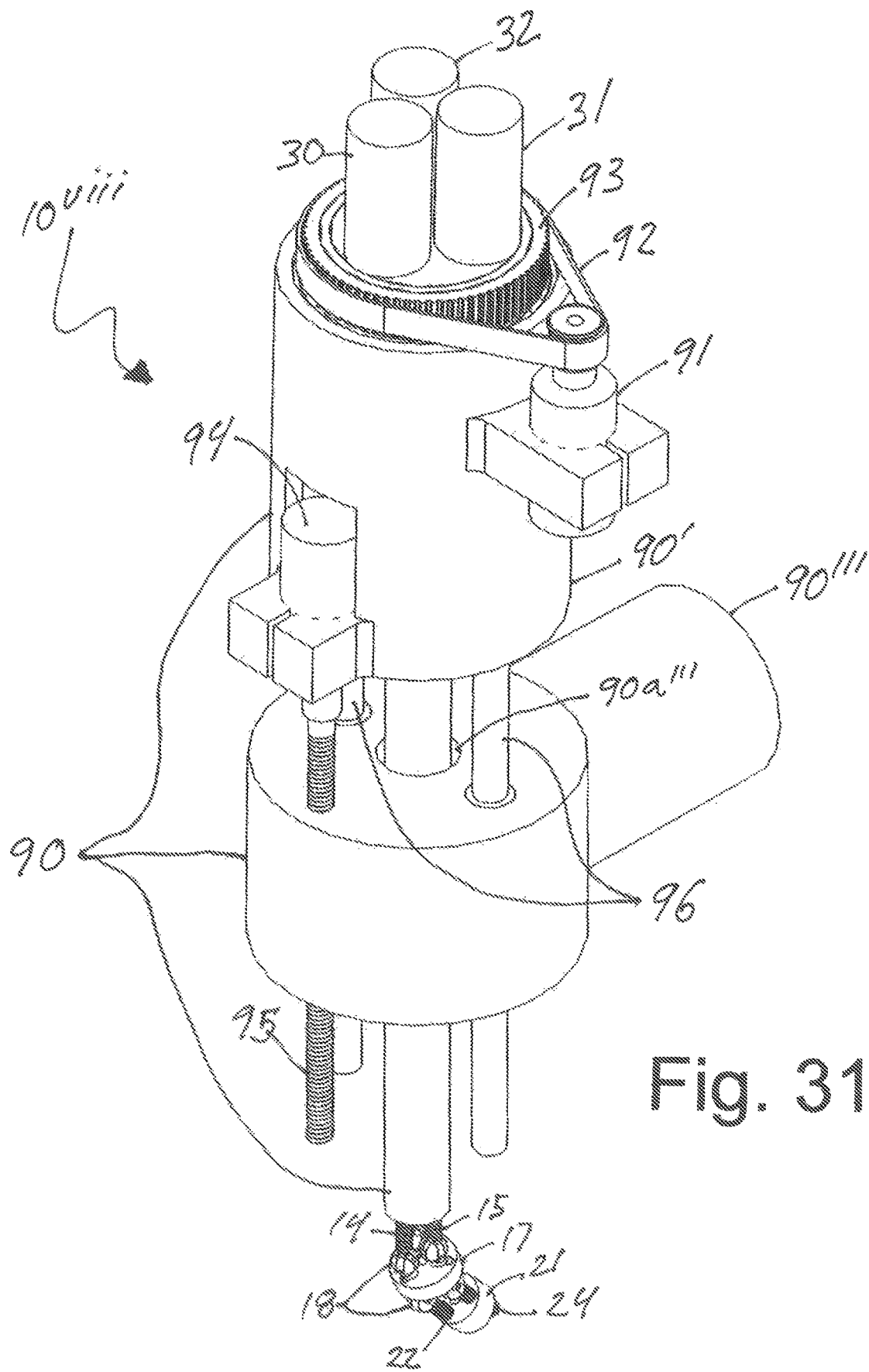
FIGS. 31 through 33 show perspective, elevation and plan views of an extended embodiment of the present invention initially shown in FIGS. 1 through 12.
Figure 32:
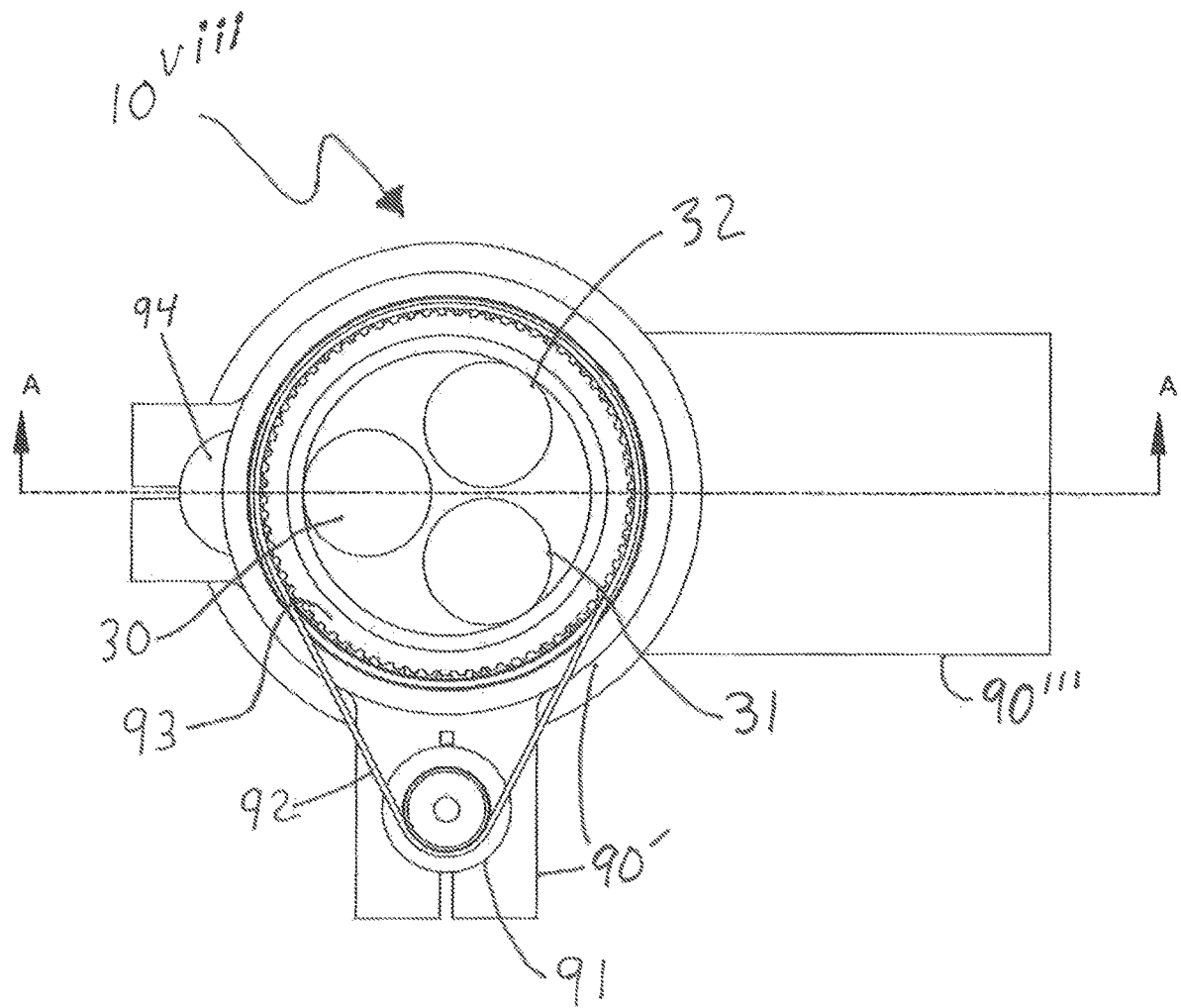
Figure 33:
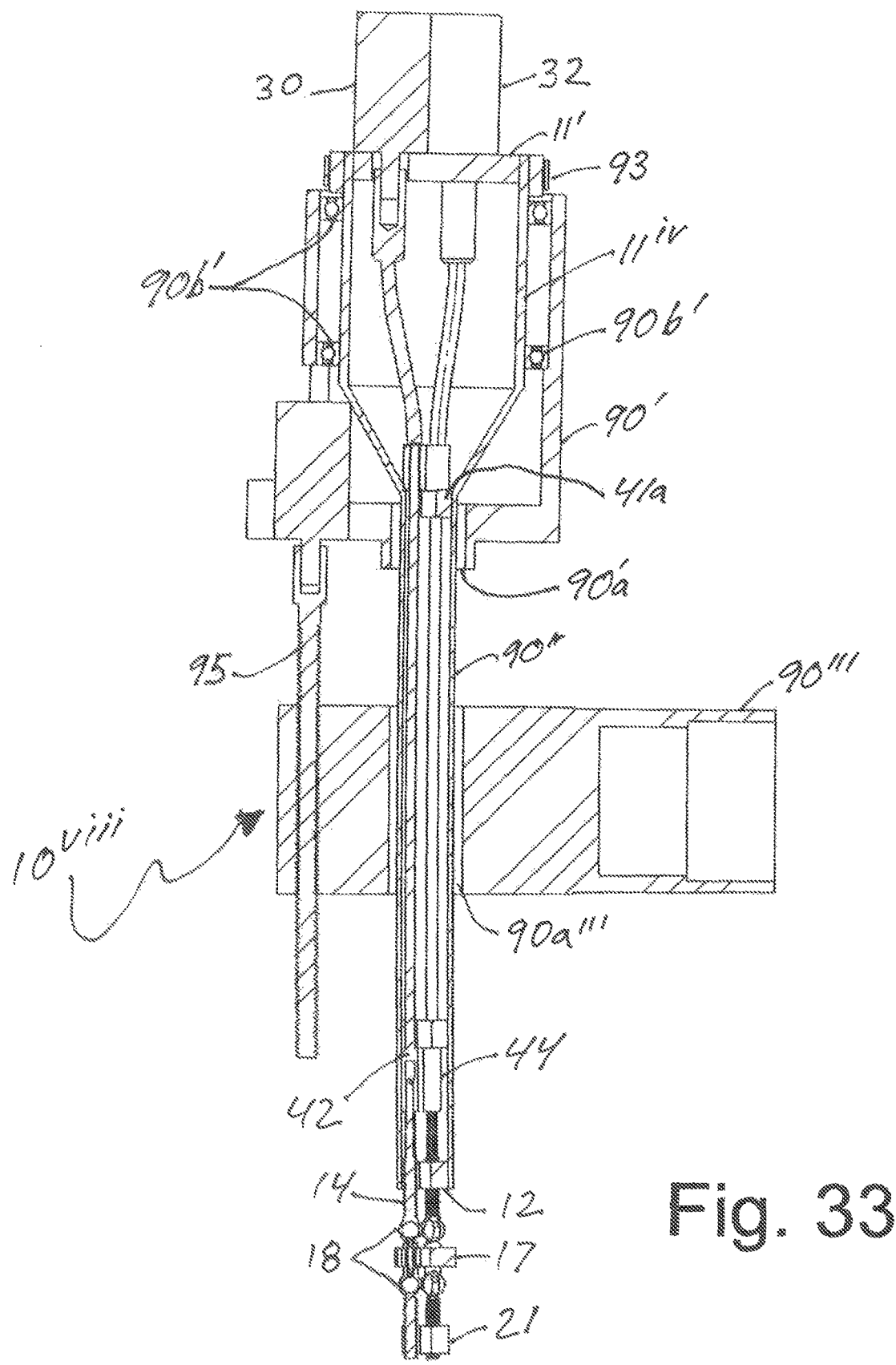

The robotic manipulators described herein can be supplemented by the addition of further position apparatus, an example of which is shown as a further robotic manipulator, $10^{viii}$, in the perspective view of FIG. 31, the plan view of FIG. 32 and the cross section view of FIG. 33 together in which robotic manipulator 10 has been used although other manipulators described herein could have instead been used. A three part encasement structure, 90, contains the portions of robotic manipulator 10 from motor mounting plate 11' through base plate 12 in a base housing, 90', a tubular sleeve arrangement, 90'' and a guide mounting structure, 90'''.

Protective cylindrical shell sleeve 11''' in a both truncated and extended version, $11^{iv}$, is affixed at its larger diameter end to motor mounting plate 11' and extended for a distance before narrowing its diameter to be affixed to a modified bushing plate, 41*a*, forming a flexible shaft guiding structure. Motors 30, 31 and 32 have their output shafts connected directly to the second cup and shaft drivers without use of the first cup and shaft drives as described previously. Sleeve version $11^{iv}$ then further extends through a bushing, 90*a'*, seated in base housing 90' and through a clearance opening, 90*a''*, in guide mounting structure, 90'', to end by being affixed to base plate 12 to complete tubular sleeve arrangement 90''. Tubular sleeve arrangement 90'', including motor mounting plate 11' with motors 30, 31 and 32 mounted therein, protective cylindrical shell sleeve truncated and extended version $11^{iv}$ and base plate 12, can be rotated together because of being mounted with base housing 90' within a bearing, 90*b'*, seated in that housing. Such rotation can be selectively made by selectively rotating the output shaft of a further motor, 91, mounted on base housing 90' at its outer surface and connected to tubular sleeve arrangement 90'' by a drive belt, 92, partially around a corrugated motor shaft ring and partially around a corrugated drive ring, 93, affixed around the outside of sleeve $11^{iv}$ directly across from motor mounting plate 11'.

In addition to the capability of rotating tubular sleeve arrangement 90'' with motors 30, 31 and 32 with respect to base housing 90', and so with respect to guide mounting structure 90''', using motor 91, selective separating and retracting movements between guide mounting structure 90''' and the remaining parts of encasement structure 90, that is, base housing 90' together with tubular sleeve arrangement 90'', by selectively rotating a further motor, 94. Motor 94 is mounted in a recess at the outer surface of base housing 90' at 90° from the mounting location of motor 91 with respect to tubular sleeve arrangement 90''. Motor 94 has a threaded shaft, 95, affixed to its output shaft which extends from there into a threaded opening in guide mounting structure 90'''. Motor 94 together with threaded shaft 95 forms a linear actuator that can change the separation between base housing 90' and guide mounting structure 90''' in selectively moving base housing 90' back and forth along tubular sleeve arrangement 90'' and along a pair of guide rods, 96, through bushings in base housing 90'. The larger movement provided by motor 94 positions tubular sleeve arrangement 90" with output plate 21 at locations where the smaller and more precise movements of just output plate 21 provided by motors 30, 31 and 32 are to be performed.

Figure 34:
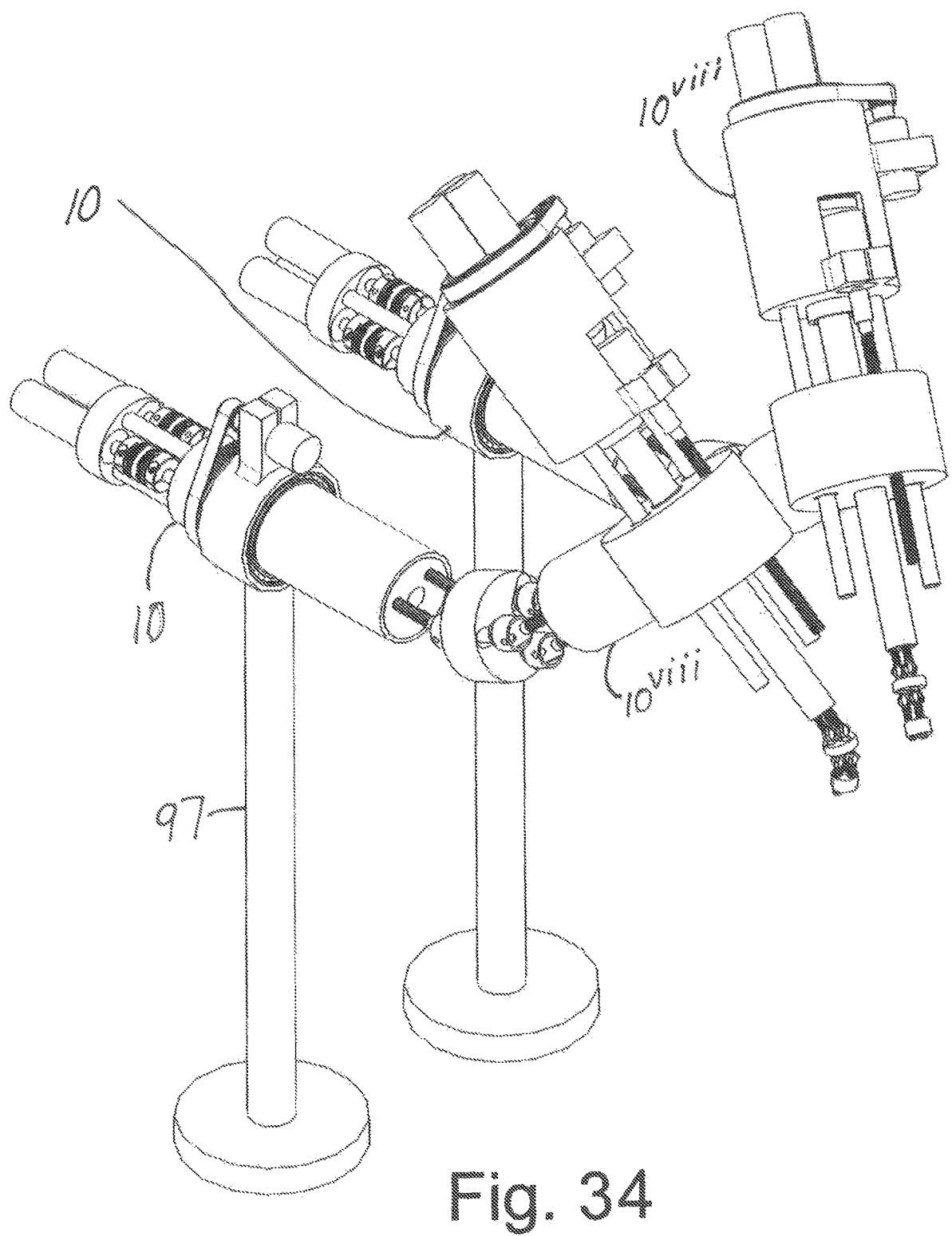
FIG. 34 shows a perspective view of another embodiment of the present invention.
Figure 35:
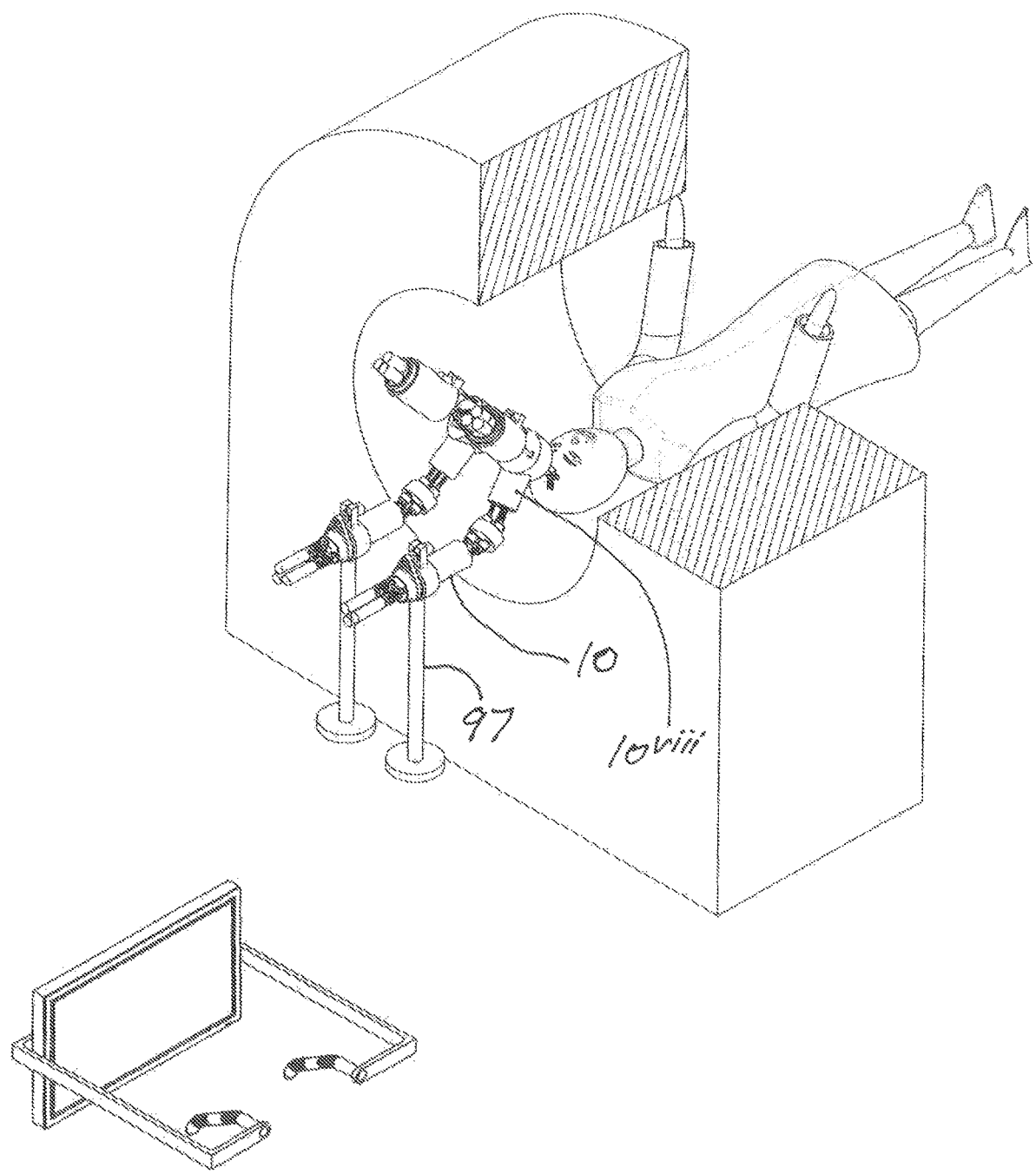
FIG. 35 shows a pictorial view of use of the embodiment of the present invention shown in FIG. 34.

Robotic manipulators are shown being used together in two pairs thereof in the perspective view of FIG. 34 with, for each pair, has a robotic manipulator 10 (also provided with the rotation capability of a robotic manipulator 10$^{viii}$ using similar components) mounted on a stand, 97, supporting on its output plate guide mounting structure 90''' of a robotic manipulator 10$^{viii}$. The larger output plate manipulator on stand 97 positions the second, smaller output plate manipulator where its smaller and more precise activities are to occur. Such an arrangement can be used, for example, in neurosurgery as indicted in the pictorial view of FIG. 35 shown in the environment of a magnetic resonance imaging (MIR) machine (requires the robotic manipulator to be constructed of nonmagnetic materials). Such a robotic manipulator arrangements are controlled by computer based control systems which can provide for a remote controller as indicated in FIG. 34.

The invention claimed is:

1. A manipulator comprising:
    a mount member;
    a base member connected to the mount member, the base member including two first threaded openings and a base aperture;
    a first link including a first link aperture and a first slot;
    a second link including a second link aperture and a second slot;
    an output member including two second threaded openings and an output aperture;
    a first motor mounted to the mount member;
    a second motor mounted to the mount member;
    a third motor mounted to the mount member;
    a first drive train connected to the first motor, the first drive train comprising:
        a first input shaft connected to the first motor, the first input shaft having a first threaded portion that extends through one of the two first threaded openings in the base member;
        a first universal joint connected to the first input shaft that extends through the first slot in the first link; and
        a first output shaft connected to the first universal joint, the first output shaft having a second threaded portion that extends through one of the two second threaded openings in the output member;
    a second drive train connected to the second motor the second drive train comprising:
        a second input shaft connected to the second motor, the second input shaft having a third threaded portion that extends through another one of the two first threaded openings in the base member;
        a second universal joint connected to the second input shaft that extends through the second slot in the second link; and
        a second output shaft connected to the second universal joint, the second output shaft having a fourth threaded portion that extends through another one of the two second threaded openings in the output member; and
    a third drive train connected to the third motor, the third drive train comprising:
        a third input shaft connected to the third motor, the third input shaft extending through the base aperture;
        a third universal joint connected to the third input shaft that extends through the first link aperture and the second link aperture; and
        a third output shaft connected to the third universal joint, the third output shaft extending through the output aperture.

2. The manipulator of claim 1, wherein the two first threaded openings in the base member are arranged to be 90 degrees apart from one another.

3. The manipulator of claim 1, wherein the mount member comprises:
    a mount plate;
    a post connected to the mount plate at a first end; and
    a bushing plate connected to a second end of the post.

4. The manipulator of claim 3, wherein the first and second motors are mounted to the mount plate and the third motor is mounted to the bushing plate.

5. The manipulator of claim 1, wherein the first input shaft of the first drive train and the second input shaft of the second drive train each includes a splined portion.

* * * * *